United States Patent
Crich et al.

(10) Patent No.: US 8,063,035 B2
(45) Date of Patent: Nov. 22, 2011

(54) TRIAZOLYL AMINOPYRIMIDINE COMPOUNDS

(75) Inventors: Joyce Z. Crich, Indianapolis, IN (US); James Robert Henry, Indianapolis, IN (US); Hong Hu, Chapel Hill, NC (US); Delu Jiang, Westfield, IN (US); Hong-Yu Li, Zionsville, IN (US); William Thomas McMillen, McCordsville, IN (US); Jason Scott Sawyer, Indianapolis, IN (US); Melissa Kate Slater, Carmel, IN (US); Yan Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 91 days.

(21) Appl. No.: 12/598,926

(22) PCT Filed: May 7, 2008

(86) PCT No.: PCT/US2008/062808
§ 371 (c)(1),
(2), (4) Date: Nov. 5, 2009

(87) PCT Pub. No.: WO2008/144223
PCT Pub. Date: Nov. 27, 2008

(65) Prior Publication Data
US 2010/0087431 A1    Apr. 8, 2010

Related U.S. Application Data

(60) Provisional application No. 60/938,347, filed on May 16, 2007.

(51) Int. Cl.
*A61K 31/381* (2006.01)
*C07D 333/16* (2006.01)
*C07D 409/14* (2006.01)

(52) U.S. Cl. .............. 514/210.2; 514/233.5; 514/252.18; 514/275; 514/359; 544/122; 544/331; 548/255

(58) Field of Classification Search .............. 514/210.2, 514/233.5, 252.18, 275, 359; 544/122, 331; 548/255
See application file for complete search history.

(56) References Cited

U.S. PATENT DOCUMENTS

2010/0130466 A1*  5/2010  Brooks et al. .............. 514/210.2

FOREIGN PATENT DOCUMENTS

| WO | WO89/07599 | 8/1989 |
|---|---|---|
| WO | WO2004063192 | 7/2004 |
| WO | WO2004089913 | 10/2004 |
| WO | WO 2006/066172 A1 * | 6/2006 |
| WO | WO2006066172 | 6/2006 |
| WO | WO2007092095 | 8/2007 |
| WO | WO2007117465 | 10/2007 |
| WO | WO2008076704 | 6/2008 |
| WO | WO2008144222 | 11/2008 |
| WO | WO2008144223 | 11/2008 |

OTHER PUBLICATIONS

Patani et al., Chem. Rev., 1996, 96, pp. 3147-3176.*

* cited by examiner

*Primary Examiner* — Susannah Chung
(74) *Attorney, Agent, or Firm* — Tina M. Tucker

(57) ABSTRACT

The present invention provides triazolyl aminopyrimidine compounds useful in the treatment of cancer.

8 Claims, No Drawings

TRIAZOLYL AMINOPYRIMIDINE COMPOUNDS

This application claims the benefit under 35 U.S.C. §371 of International Application No. PCT/US2008/062808 filed May 7, 2008 which claims benefit under 35 U.S.C. §119(e) of U.S. Ser. No. 60/938,347 filed May 16, 2007.

Plk1 belongs to a small family of protein kinases characterized by a phosphoserine/threonine binding domain known as the polo box domain. Plk1 plays a central role in the regulation of the cell cycle. Among other functions, Plk1 is thought to regulate initiation, progression, and exit from mitosis, the stage when cancer cells divide. Consequently, blocking Plk1 in cancer cells prevents their division or mitosis.

Potent anticancer agents have been identified that interfere with mitosis such as the vinca alkaloids (NAVELBINE®), taxoids (TAXOTERE®) and topoisomerase II inhibitors (ADRIAMYCIN®). VELCADE® is an antineoplastic agent that inhibits the 26S proteosome. However, these drugs cause considerable side effects upon normal, non-dividing cells. Plk inhibitors specifically target dividing cells and may be able to avoid the undesirable toxicities.

Inhibitors of Plk1 are known in the art. See for example, WO 06/066172. Additionally, WO 06/021548 discloses certain dihydropteridinone analogs (e.g., BI-2536) as inhibitors of Plk1. Currently, BI-2536 is in phase II clinical trials but has high clearance (CL>1000 mL/min) and is dose limited by myelosupression in man. There is still a need for further compounds that inhibit Plk1 which possess improved potency or pharmacokinetic properties.

The present invention provides novel triazolyl aminopyrimidine compounds believed to have clinical use for treatment of cancer through inhibiting Plk1. Certain of these compounds are believed to have improved potency over compounds disclosed in WO 06/066172. Additionally, certain of the compounds of the present invention are believed to have improved pharmacokinetic properties, for example, clearance, over BI-2536. Further, due to the oral bioavailability of the compounds of the present invention that were tested, it is believed that certain of these compounds could be dosed orally.

The present invention provides compounds of Formula I:

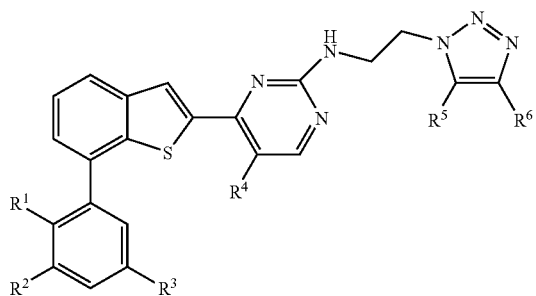

wherein:

$R^1$ is methyl, methoxy, hydroxy, amino, chloro, amino($C_1$-$C_4$ alkyl), dimethylamino($C_1$-$C_2$ alkyl), ($C_1$-$C_2$ alkyl)amino ($C_1$-$C_2$ alkyl), aminocarbonyl($C_1$-$C_3$ alkyl), 1-((1-amino)ethylcarbonylamino)ethyl, 2-(N-methylamino)ethoxy, 2-cyanoprop-2-yl, (2-hydroxy-2-methyl)-1-propyloxy, (2-hydroxy)ethylaminocarbonylmethyl, (1-fluoro)-(2-amino)ethyl, (1-fluoro)-(1-methyl)-(2-amino)ethyl, difluoromethyl, 1-((2,2-difluoro)ethylamino)ethyl, difluoromethylcarbonyl, trifluoromethylcarbonyl, (1-amino)-(2,2,2-trifluoro)ethyl, (1-methylamino)-(2,2,2-trifluoro)ethyl, (1-hydroxy)-(2,2,2-trifluoro)ethyl, 2-(amino)ethoxy, 2-(hydroxy)ethoxy, 1-((N-(2-hydroxy)ethyl)-(N-methyl)-amino) ($C_1$-$C_2$ alkyl), 4-(hydroxy)piperidin-1-yl-methyl, 1-(piperazin-1-yl)ethyl, 2-(hydroxy)ethylsulfonyl, 1-(amino) cyclopropyl, 1-(methylamino)cyclopropyl, 1-amino (cyclobutyl), 1-aminocyclopent-2-yl, cyclopentanone-2-yl, tetrahydrofur-2-yl, pyrrolidin-2-yl, aziridin-2-yl, or (morpholin-4-yl)methyl;

$R^2$ is hydrogen or amino provided that if $R^2$ is amino, $R^1$ and $R^2$ form a pyrrole ring fused to the phenyl; or if $R^1$ is amino, $R^1$ and $R^2$ can form either a pyrrole or a pyridine ring fused to the phenyl;

$R^3$ is hydrogen chloro, or fluoro;

$R^4$ is hydrogen, methyl, chloro, or fluoro;

$R^5$ is hydrogen, hydroxymethyl, or methyl; and $R^6$ is hydrogen, hydroxymethyl, or methyl; or a pharmaceutically acceptable salt thereof.

The present invention provides a method of treating cancer selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers in a mammal comprising administering to a mammal in need of such treatment an effective amount of a compound of Formula I or a pharmaceutically acceptable salt thereof.

The present invention also provides a pharmaceutical composition comprising a compound of Formula I or a pharmaceutically acceptable salt thereof, in combination with a pharmaceutically acceptable excipient, carrier, or diluent.

This invention also provides a compound of Formula I or a pharmaceutically acceptable salt thereof for use as a medicament. Additionally, this invention provides use of a compound of Formula I or a pharmaceutically acceptable salt thereof in the manufacture of a medicament for treating cancer. In particular these cancers are selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers. Furthermore, this invention provides a pharmaceutical composition for treating cancer selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers comprising a compound of Formula I or a pharmaceutically acceptable salt thereof as an active ingredient.

The present invention also provides compounds of the Formula:

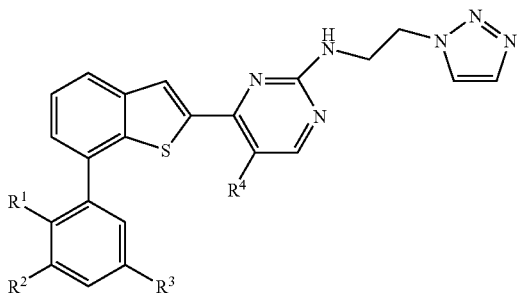

wherein:

$R^1$ is methyl, methoxy, hydroxy, amino, chloro, amino($C_1$-$C_2$ alkyl), dimethylaminomethyl, ($C_1$-$C_2$ alkyl)amino($C_1$-$C_2$ alkyl), aminocarbonylmethyl, 2-(N-methylamino)ethoxy, (2-hydroxy-2-methyl)-1-propyloxy, difluoromethyl, 2-(amino)ethoxy, 2-(hydroxy)ethoxy, 4-(hydroxy)piperidin-1-yl-methyl, [N-(2-hydroxy)ethyl-N-methyl]-aminomethyl, 2-(hydroxy)ethylsulfonyl, 1-(amino)cyclopropyl, tetrahydrofur-2-yl, or (morpholin-4-yl)methyl;

$R^2$ is hydrogen or amino provided that if $R^2$ is amino, $R^1$ and $R^2$ form a pyrrole ring fused to the phenyl; or if $R^1$ is amino, $R^1$ and $R^2$ can form either a pyrrole or a pyridine ring fused to the phenyl;

$R^3$ is hydrogen or halo; and $R^4$ is hydrogen or halo; or a pharmaceutically acceptable salt thereof.

The general chemical terms used in the formulae above have their usual meanings. For example, the term "($C_1$-$C_4$ alkyl)" means methyl, ethyl, n-propyl, isopropyl, n-butyl, isobutyl, sec-butyl, and tert-butyl. The term "($C_1$-$C_3$ alkyl)" is included within the meaning of "($C_1$-$C_4$ alkyl)" and means methyl, ethyl, n-propyl, and isopropyl. The term "($C_1$-$C_2$ alkyl)" is included within the term "($C_1$-$C_4$ alkyl)" and means methyl and ethyl.

The term "halo" means fluoro, chloro, bromo, and iodo.

When a substituent is attached through an alkyl group such as ethyl, n-propyl, isopropyl, n-butyl, isobutyl, sec-butyl, or tert-butyl in the terms "amino($C_1$-$C_4$ alkyl)" or "dimethylamino($C_1$-$C_2$ alkyl)" or "($C_1$-$C_2$ alkyl)amino($C_1$-$C_2$ alkyl)", the attachment of the substituent may be through any carbon of the alkyl. Using aminoethyl [amino($C_2$ alkyl)] as an illustration, the following

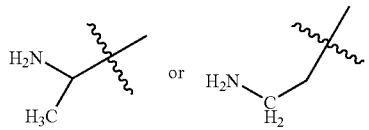

connectivities are intended.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

Preferred are compounds of Formula I wherein:

a) $R^1$ is amino($C_1$-$C_4$ alkyl);

b) $R^1$ is 1-(amino)ethyl;

c) $R^2$ is hydrogen;

d) $R^3$ is fluoro;

e) $R^4$ is fluoro;

f) $R^5$ is hydrogen or methyl;

g) $R^5$ is methyl;

h) $R^6$ is hydrogen;

i) $R^1$ is amino($C_1$-$C_4$ alkyl), dimethylamino($C_1$-$C_2$ alkyl), ($C_1$-$C_2$ alkyl)amino($C_1$-$C_2$ alkyl), aminocarbonyl($C_1$-$C_3$ alkyl), 1-((1-amino)ethylcarbonylamino)ethyl, 2-cyanoprop-2-yl, (2-hydroxy)ethylaminocarbonylmethyl, (1-fluoro)-(2-amino)ethyl, (1-fluoro)-(1-methyl)-(2-amino)ethyl, difluoromethyl, 1-((2,2-difluoro)ethylamino)ethyl, (1-amino)-(2,2,2-trifluoro)ethyl, (1-methylamino)-(2,2,2-trifluoro)ethyl, (1-hydroxy)-(2,2,2-trifluoro)ethyl, 1-((N-(2-hydroxy)ethyl)-(N-methyl)-amino)($C_1$-$C_2$ alkyl), 4-(hydroxy)piperidin-1-yl-methyl, 1-(piperazin-1-yl)ethyl, or (morpholin-4-yl)methyl;

j) $R^1$ is amino($C_1$-$C_4$ alkyl), dimethylamino($C_1$-$C_2$ alkyl), ($C_1$-$C_2$ alkyl)amino($C_1$-$C_2$ alkyl), (2-hydroxy)ethylaminocarbonylmethyl, or (morpholin-4-yl)methyl; and $R^6$ is hydrogen;

k) $R^1$ is amino($C_1$-$C_4$ alkyl), dimethylamino($C_1$-$C_2$ alkyl), ($C_1$-$C_2$ alkyl)amino($C_1$-$C_2$ alkyl), or (morpholin-4-yl)methyl;

$R^3$ is fluoro;

$R^4$ is fluoro;

$R^5$ is hydrogen or methyl; and $R^6$ is hydrogen;

l) $R^1$ is amino($C_1$-$C_4$ alkyl), dimethylamino($C_1$-$C_2$ alkyl), or ($C_1$-$C_2$ alkyl)amino($C_1$-$C_2$ alkyl);

$R^3$ is fluoro;

$R^4$ is fluoro;

$R^5$ is hydrogen or methyl; and $R^6$ is hydrogen;

m) The is compound of Claim 1 wherein $R^1$ is 1-(amino)ethyl, $R^3$ is fluoro, $R^4$ is fluoro, $R^5$ is hydrogen, and $R^6$ is hydrogen; and n) The compound of Claim 1 wherein $R^1$ is 1-(amino)ethyl, $R^3$ is fluoro, $R^4$ is fluoro, $R^5$ is methyl, and $R^6$ is hydrogen.

The schemes together with the preparations and examples illustrate the synthesis of compounds of the present invention.

Scheme I

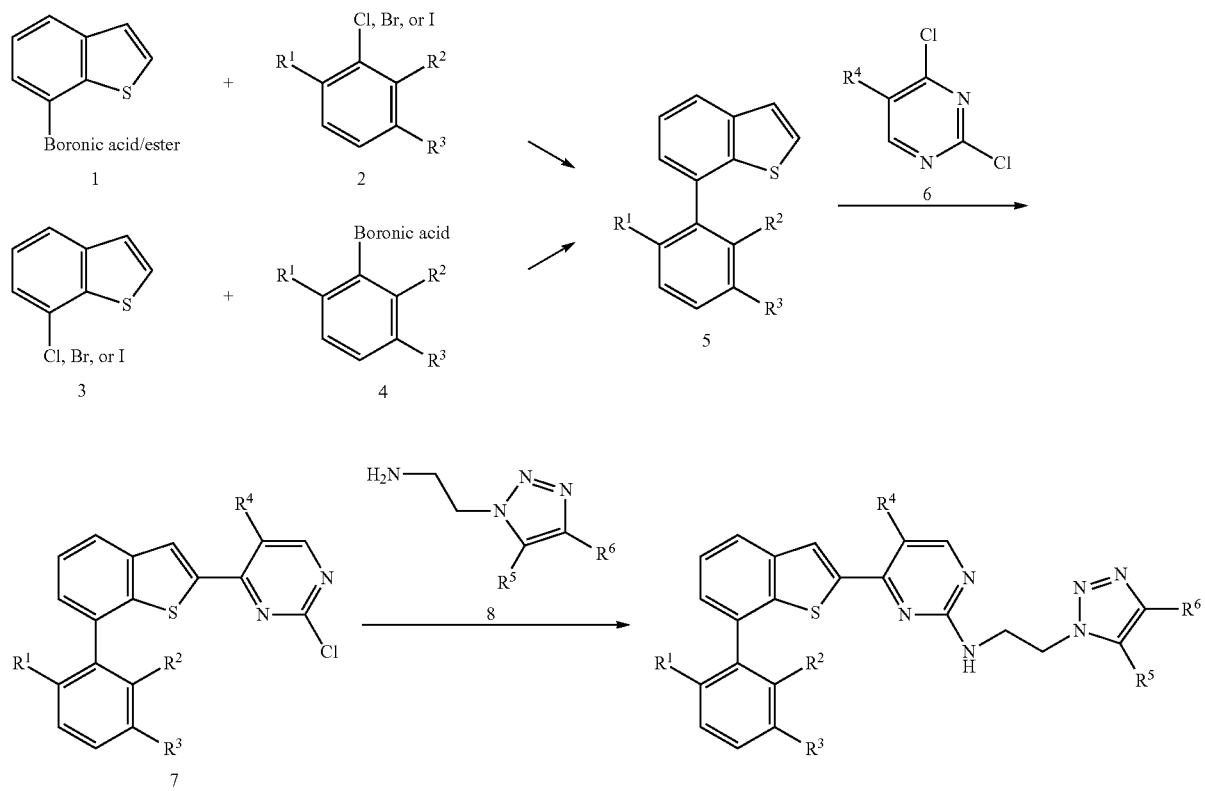

Compound 5 in Scheme I is prepared by a palladium (0) coupling reaction between either starting material 1 with 2, or starting material 3 with 4. A suitable palladium catalyst, such as tetrakis(triphenylphosphine)-palladium(0) or [1,1'-bis(diphenyl-phosphino)ferrocene]dichloropalladium(II) complex with DCM (1:1) [Pd(dppf)Cl₂]. Pd(dppf)Cl₂ is used in the presence of base, such as sodium or potassium carbonate. The reactions are carried out in a solvent, such as tetrahydrofuran (THF), dioxane, and water, generally, at temperatures of from about 100° C. to 150° C. using an oil bath or a microwave reactor.

Compound 5 is lithiated with lithium diiopropylamide in tetrahydrofuran (THF) and triisopropylborate in situ forming a benzo[b]thiophene boronate species followed by a palladium (0) coupling reaction with a 2,4-dichloropyrimidine (Compound 6) giving Compound 7. The boronate is generally formed at a low temperature, such as −78° C. The coupling reaction is followed immediately with conditions as described above for preparing Compound 5.

Compounds of the present invention are then prepared via a nucleophilic displacement reaction where Compound 7 is reacted with Compound 8. Such reactions are carried out in a solvent, such as, n-butanol, dioxane, and N-methylpyrolidin-2-one (NMP). The reactions are carried out at temperatures of from about 120° C. to 150° C. using an oil bath or a microwave reactor. About 2 equivalents of 2-(amino-ethyl)-1,2,3-triazole (Compound 8) are used. Amine bases, such as triethyl amine and diisopropylethyl amine are used as acid scavengers.

Scheme II

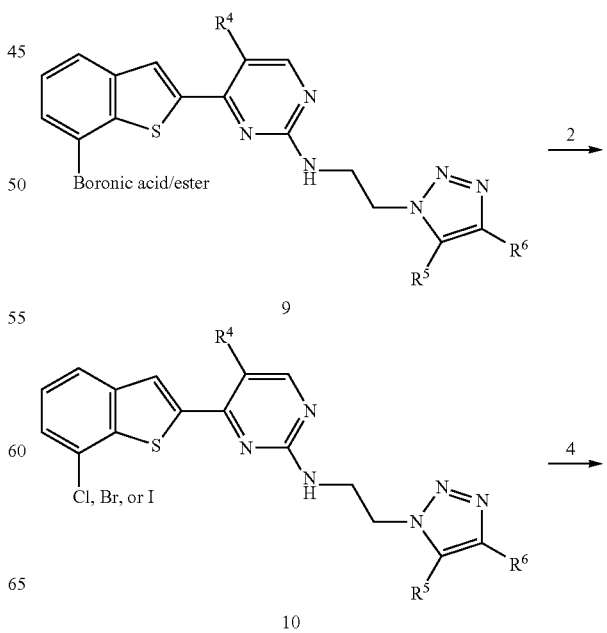

-continued

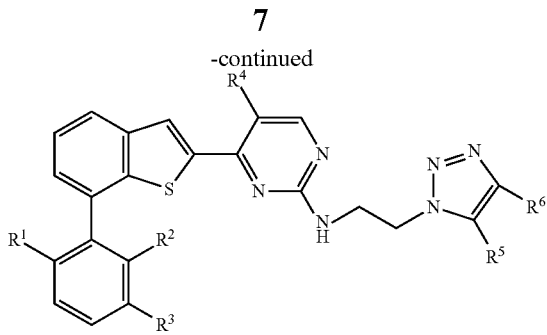

Alternately, compounds of the present invention can be prepared by the Suzuki reaction between starting materials 2 and 9 or 4 and 10 with conditions described above.

Since two coupling reactions are employed in the synthesis of compounds of the present invention, starting materials 9 and 10 of Scheme II represent a reverse coupling order by comparison with Scheme I.

The skilled artisan will appreciate that not all of the substituents in the compounds of the present invention will tolerate certain reaction conditions employed to synthesize the compounds. These moieties may be introduced at a convenient point in the synthesis, or may be protected and then deprotected as necessary or desired. The skilled artisan will appreciate that protecting groups may be introduced or removed at any convenient point in the synthesis of the compounds of the present invention. Methods for introducing and removing nitrogen and oxygen protecting groups are well known in the art; see, for example, Greene and Wuts, Protective Groups in Organic Synthesis, 3$^{rd}$ Ed., John Wiley and Sons, New York, Chapter 7 (1999). For an example chiral synthesis, (R)-tert-butylsulfinamine can be used both 1) as a chiral auxiliary via condensation with aldehydes to form sulfinimines followed further by stereoselective reactions, e.g., with (trifluoromethyl)trimethylsilane to form protected diastereomeric sulfinamides and 2) as an easily removable amino protection group once a diastereomeric sulfinamide has been isolated. Some of the examples of the present invention are prepared from other examples of the present invention. Furthermore, the skilled artisan will appreciate that in many circumstances, the order in which the moieties are introduced is not critical. The particular order of steps required to produce the compounds of the present invention can be dependent upon the particular compound being synthesized, the starting compound, and the relative lability of the substituted moieties.

Some the compounds of the present invention contain asymmetric centers. In these instances, the enantiomers as well as the racemate are contemplated in the present invention. ChemDraw® version 10.0 was used in generating Example names.

PREPARATION 1

2-Benzo[b]thiophen-7-yl-4,4,5,5-tetramethyl-[1,3,2]dioxaborolane

Combine 7-bromo-benzo[b]thiophene (426 mg, 2 mmol), bis-(pinacolato)-diboron (756 mg, 3 mmol), Pd(dppf)Cl$_2$ (81 mg, 0.1 mmol), potassium acetate (294 mg, 3 mmol) in dimethyl sulfoxide (DMSO) (10 mL) in a flask. Bubble nitrogen through the mixture for 5 minutes (min). Seal the flask and place it into an oil bath to heat at 100° C. for 4 hours (h). Dilute the mixture with chloroform/isopropyl alcohol (IPA) (3/1). Wash the solution with aqueous saturated sodium chloride. Dry over sodium sulfate. Concentrate the solution in vacuo to a dark residue. Purify by column chromatography (hexane→20% ethyl acetate in hexane) to give the title compound as a colorless solid (342 mg, 66%). MS (ES) m/z 261 [M+1]$^+$.

PREPARATION 2

Benzo[b]thiophene-7-boronic acid

Combine 7-bromobenzo[b]thiophene (300 g, 1.41 mmol) and tri-isopropylborate (403.6 g, 2.15 mmol) in anhydrous THF (4 L) in a 12-L Morton flask fitted with a mechanical stirrer and cool under nitrogen in a dry-ice/acetone bath to −70° C. Add n-butyl lithium (1.6 M in hexane, 714 g, 1.68 mmol) dropwise at such a rate as to keep the internal temperature less than −67.5° C. After the addition is complete allow the reaction mixture to stir at this temperature for 1 h. Remove the cooling bath and slowly add 4 L of water, which causes the temperature to rise to about −5° C. Next, add concentrated HCl (75 mL) until the pH of the solution is about pH=2. Allow the slurry to stir for 1 h. Add sufficient 5 N aqueous NaOH to adjust the pH of the mixture to about pH=12 and transfer to a 22-L bottom-drop funnel Separate and save the lower aqueous layer. Dilute the upper organic layer with 4 L of methyl-tert-butyl ether and extract with 1 L of 5 N aqueous NaOH. Separate the aqueous layer, combine with the previous aqueous extract and place back in the separatory funnel Wash the aqueous layer with additional methyl-tert-butyl ether (4 L). Again, separate the aqueous layer and transfer to a 12-L, 3-neck round bottom flask fitted with a mechanical stirrer. Cool the solution to +5° C. with an ice-water bath. Add concentrated HCl slowly until the pH of the solution is about pH=2. Stir the mixture for 30 minutes and then filter off the resulting solid. Rinse the solid on the funnel twice with 2 L of water and allow to air-dry for 30 min. Place the solid in a vacuum oven at 50° C. and dry under vacuum overnight. The dried solid is slurried with 2 L of n-heptane for 30 min to remove the yellow color. Again filter off the solid, air-dry for 30 min and then vacuum-dry at 40° C. overnight to give the title compound (188.8 g, 75%) as a white solid. $^1$H NMR (400 MHz, CD$_3$OD) δ 7.86 (d, J=8 Hz, 1H), 7.49-7.57 (m, 2H), 7.30-7.39 (m, 2H).

PREPARATION 3

1-(2-Bromo-phenyl)-ethanone oxime

Combine 1-(2-bromo-phenyl)-ethanone (4.5 g, 22.6 mmol), 50% hydroxylamine in water (2.3 g, 69.6 mmol) and 1 mL of acetic acid in 15 mL of dioxane in a pressure vessel. Seal the vessel and heat the mixture in an oil bath for 3 h at 150° C. Cool the mixture to room temperature (RT). Dilute with chloroform/IPA (3/1), wash with water and aqueous saturated sodium chloride. Separate the layers and dry the organic layer over sodium sulfate. Concentrate in vacuo to give the crude product. Purify by column chromatography (20% THF in dichloromethane (DCM) to give the title compound (4.0 g, 83%). MS (ES) m/z 214/216 [M+1]$^+$.

Prepare the following intermediate with procedures similar to those described above:

| Prep | Compound Name | MS (ES) m/z [M + 1]$^+$ |
|---|---|---|
| 4 | 1-(2-Bromo-4-fluoro-phenyl)-ethanone oxime | 232/234 |

PREPARATION 5

1-(2-Bromo-4-fluoro-phenyl)-ethylamine

Cool a solution of sodium borohydride (3.1 g, 86 mmol) and titanium tetrachloride (1 M in toluene, 43 mL, 43 mmol) in 40 mL of dry 1,2-dimethoxyethane to 0° C. under $N_2$. Add 1-(2-bromo-phenyl)-ethanone oxime (4.6 g, 21.5 mmol) to the above solution dropwise. Stir the mixture overnight at RT. Quench the reaction with 200 mL of water. Basify the mixture with ammonium hydroxide. Extract the crude product into toluene and ethyl acetate. Separate the layers and dry the organic layer over sodium sulfate. Concentrate in vacuo to give the crude product (4.0 g, 100%). MS (ES) m/z 200/202 $[M+1]^+$.

Prepare the following intermediates with procedures similar to those described above:

| Prep | Compound Name | MS (ES) m/z $[M + 1]^+$ |
|---|---|---|
| 6 | 1-(2-Bromo-4-fluoro-phenyl)-ethylamine | 218/220 |
| 7 | 2-(2-Bromo-4-fluoro-phenyl)-ethylamine | 218/220 |

PREPARATION 8

2-(2-Bromo-4-chlorophenyl)-2-fluoroacetonitrile

Add 2-bromo-4-chloro-benzaldehyde (3.5 g, 16 mmol) in DCM (6 mL) to a flask that contains zinc iodide (8 mg). Stir the mixture at RT for 30 min. Cool the mixture to 0° C. with an ice-water bath. Add trimethylsilylcyanide (2.14 mL, 15.99 mmol) to the vigorously stirred mixture. Remove the cooling bath and stir at RT for 18 h. Add DCM (20 mL) and cool the mixture to 0° C. Add a solution of diethylaminosulfurtrifluoride (2.32 mL, 18 mmol) in DCM (8 mL) to the previous reaction mixture and stir the mixture overnight. Pour the reaction mixture into ice-water (50 mL) and separate the organic layer. Wash the organic layer with water, 0.5 N HCl, water, saturated $NaHCO_3$, and water. Dry over magnesium sulfate. Remove the organic solvent to give the crude product. Purify by column chromatography (hexane/ethyl acetate, 10:1) to give the title compound (2.40 g, 74%). MS (GC) 249 $[M]^+$.

Prepare the following intermediate with a procedure similar to the one described above:

| Prep | Compound Name | MS (GS) $[M]^+$ | Comments |
|---|---|---|---|
| 9 | 2-(2-Bromo-4-fluorophenyl)-2-fluoropropanenitrile | 247 | From 1-(2-bromo-4-fluorophenyl)ethanone |

PREPARATION 10

2-(2-Bromo-4-chlorophenyl)-2-fluoroethanamine, hydrochloride

Dissolve 2-(2-bromo-4-chlorophenyl)-2-fluoroacetonitrile (2.45 g, 9.86 mmol) in THF (50 mL). Cool the mixture to 0° C., then add $BH_3$-THF complex (1 N, 20 mL, 20 mmol), and stir overnight. Add ethanol (5 mL) and then adjust to acidic with an ethanolic HCl solution. After removing the solvent, add DCM (20 mL) to the solid. Filter and wash with DCM, and dry to give the title compound as the HCl salt. MS (ES) m/z 254 $[M+1]^+$.

Prepare the following intermediate with a procedure similar to the one described above:

| Prep | Compound Name | MS (ES) m/z $[M + 1]^+$ |
|---|---|---|
| 11 | 2-(2-Bromo-4-fluorophenyl)-2-fluoropropan-1-amine, hydrochloride | 250.0 |

PREPARATION 12

2-(2-Bromo-4-fluorophenyl)-2-methylpropanenitrile

Add sodium hydride (1 g, 42.1 mmol) to a stirred solution of (2-bromo-4-fluoro-phenyl)-acetonitrile (3 g, 14 mmol) in 10 mL of dimethyl formamide (DMF) at 0° C. Stir the mixture at 0° C. to RT for half an hour. Add methyl iodide (6 g, 42 mmol). Stir for another 30 min. Quench the reaction with water. Extract the product into DCM. Dry the organic phase over sodium sulfate and concentrate to give an oily residue. Purify the residue by flash column chromatography (FCC) (hexane to 20% ethyl acetate in hexane as gradient elute) to give the title compound as a white solid (2.2 g, 65%). $^1$H NMR (400 MHz, $CDCl_3$) δ 7.41-7.47 (m, 2H), 7.03-7.08 (m, 1H), 1.88 (s, 6H).

PREPARATION 13

2-(2-Bromo-4-fluorophenyl)-2-methylpropanoic acid

Mix 2-(2-bromo-4-fluoro-phenyl)-2-methyl-propionitrile (1 g, 4.13 mmol) and 1,4,7,10,13,16-hexaoxacyclooctadecane (18-crown-6) (100 mg, 1% wt) with sodium hydroxide (10 M, 20 mL, 200 mmol) in ethanol (5 mL). Heat the mixture to reflux for 3 h. Quench the reaction with 1 N HCl. Extract the product with chloroform. Dry the organic phase over sodium sulfate and concentrate to give an oily residue. Purify the residue by FCC (10% methanol in DCM as eluant) to give the title compound as a yellow solid (1 g, 93%). MS (ES) m/z 260/262 $[M+1]^+$.

PREPARATION 14

2-(2-Bromo-4-fluorophenyl)-2-methylpropan-1-amine

Add borane-THF complex (2 M in THF, 10 mL, 20 mmol) to a stirred solution of 2-(2-bromo-4-fluoro-phenyl)-2-methyl-propionitrile (0.8 g, 3.30 mmol) in 10 mL of THF at 0° C. Stir the mixture at 0° C. to RT over the weekend. Quench the reaction with diluted ammonium hydroxide. Extract the product with chloroform. Dry the organic phase over sodium sulfate and concentrate to give the title compound (0.8 g, 99%). MS (ES) m/z 246/248 $[M+1]^+$.

PREPARATION 15

1-(2-Bromo-4-fluorophenyl)-2,2,2-trifluoroethanol

Charge 2-bromo-4-fluoro-benzaldehyde (6.1 g, 30.1 mmol) and trifluoromethyl trimethylsilane (5.4 g, 36.1 mmol)

in THF (50 mL) in a 100-mL round bottom flask. Cool the solution to 0° C. under $N_2$. Add $Bu_4NF$ (0.3 g, 1.20 mmol). Stir the mixture at 0° C. for another hour. Add hydrogen chloride (40 mL, 1 M, 40 mmol) to the mixture. Stir the mixture at RT overnight. Dilute the reaction mixture with chloroform. Wash the organic layer with water/aqueous saturated sodium chloride, dry over sodium sulfate, and concentrate in vacuo to give the crude product. Purify by FCC (hexanes/ethyl acetate, 4/1) to give the title compound as a yellow oil (7.40 g, 90%). MS (ES) m/z 273/275 $[M+1]^+$.

PREPARATION 16

1-(2-Bromo-4-fluorophenyl)-2,2,2-trifluoroethanone

Add 1-(2-bromo-4-fluoro-phenyl)-2,2,2-trifluoro-ethanol (12 g, 43.9 mmol) in 20 mL DCM to a stirred suspension solution of 3,3,3-triacetoxy-3-iodophthalide (52 g, 122.6 mmol) and 18-crown-6 (0.6 g) in DCM (400 mL). Stir the mixture at RT for 4 h and pour into a solution of $NaHCO_3$/$NaS_2O_3$. Wash the organic layer with water, dry over sodium sulfate, and concentrate in vacuo. Purify the resulting crude product by FCC (20% ethyl acetate in hexane as the eluant) to give the title compound as a pale yellow oil (9 g, 76%). $^1$H NMR (400 MHz, $CDCl_3$) δ 7.77 (m, 1H), 7.51 (m, 1H), 7.20 (m, 1H).

PREPARATION 17

1-(2-Bromo-4-fluorophenyl)propan-1-ol

Add ethylmagnesium bromide (1 M in ether, 8.37 mL, 8.37 mmol) at 0° C. under nitrogen to a solution of 2-bromo-4-fluorobenzaldehyde (1 g, 4.93 mmol) in diethyl ether (15 mL). Stir the mixture for 1 h at RT. Add water slowly followed by adjusting the mixture to acidic conditions with 2 M HCl. Extract the product with chloroform/IPA (3/1). Dry over sodium sulfate. Concentrate the solution in vacuo to a yellow oil. Purify by column chromatography (30% ethyl acetate in hexane) to give the title compound as a colorless oil (1.1 g, 96%). $^1$H NMR (400 MHz, $CD_3Cl$) δ 0.99 (t, J=7.2 Hz, 3H), 1.75 (m, 2H), 4.99 (m, 1H), 7.03 (m, 1H), 7.25 (m, 1H), 7.53 (m, 1H).

Prepare the following intermediates with procedures similar to those described above:

| Prep | Compound Name | MS (ES) m/z $[M + 1]^+$ | comments |
|---|---|---|---|
| 18 | 2-(2-Bromo-4-fluoro-phenyl)propan-2-ol | 233/235 | From 1-(2-bromo-4-fluorophenyl)ethanone and methyl magnesium bromide |
| 19 | 1-(2-Bromo-4-fluorophenyl)-2-methylpropan-1-ol | 247/249 | |

PREPARATION 20

N-(2-(2-Bromo-4-fluorophenyl)propan-2-yl)formamide

Add 98% sulfuric acid drop-wise (3 g, 31 mmol) to a mixture of 2-(2-bromo-4-fluoro-phenyl)-propan-2-ol (2.4 g, 10.30 mmol) and trimethylsilyl cyanide (2.04 g, 59 mmol) in a 25-mL round bottom flask under $N_2$ at −20° C. Move the flask out of the cooling bath and stir the mixture at RT overnight. Dilute the mixture with ice-water and neutralize with ammonium hydroxide to pH=8. Extract the product with chloroform/IPA (3/1, 100 mL). Wash the organic phase with water/aqueous saturated sodium chloride, dry over sodium sulfate, and concentrate in vacuo to give the crude product. Purify by FCC (20% THF in DCM as elute) to give the title compound as a white solid (2 g, 75%). MS (ES) m/z 260/262 $[M+1]^+$.

PREPARATION 21

1-(1-Azido-2,2,2-trifluoroethyl)-2-bromo-4-fluorobenzene

Add 4,5-dichloro-3,6-dioxocyclohexa-1,4-diene-1,2-dicarbonitrile (5 g, 22 mmol) to a stirred solution of triphenylphosphine (5.76 g, 22 mmol) in 50 mL of DCM portionwise. After stirring for 2 min, add tetra-N-butyl ammonium azide (6.25 g, 22 mmol). Add a solution of 1-(2-bromo-4-fluorophenyl)-2,2,2-trifluoroethanol (4 g, 14.7 mmol) in 10 mL of DCM into the above mixture. Stir the mixture at RT for 1 h and concentrate to about 30 mL. Load the mixture onto a silica column. Elute with hexane to 20% ethyl acetate in hexane to give the title compound as a brown oil (0.8 g, 18%). MS (ES) m/z 298/300 $[M+1]^+$.

Prepare the following intermediates with procedures similar to those described above:

| Prep | Compound Name | MS (ES) m/z $[M + 1]^+$ |
|---|---|---|
| 22 | (R)-1-(1-Azidoethyl)-2-bromobenzene | 226/228 |
| 23 | 1-(1-Azido-2-methylpropyl)-2-bromo-4-fluorobenzene | 272/274 |

PREPARATION 24

1-(2-Bromo-4-fluorophenyl)-2,2,2-trifluoroethanamine

Add Raney Nickel (1.58 g, 26.8 mmol) to a solution of 1-(1-azido-2,2,2-trifluoro-ethyl)-2-bromo-4-fluoro-benzene (0.8 g, 2.68 mmol), formic acid (1.24 g, 26.8 mmol), and hydrazine (0.86 g, 26.8 mmol) in 10 mL of ethanol. Stir the mixture at RT for 1 h and filter off the excess Nickel. Dilute the mother liquor with water and extract with chloroform. Dry the organic layer over sodium sulfate and concentrate to give the title compound as a brown oil (0.73 g, 100%). MS (ES) m/z 272/274 $[M+1]^+$.

Prepare the following intermediate with procedure similar to those described above:

| Prep | Compound Name | MS (ES) m/z $[M + 1]^+$ |
|---|---|---|
| 25 | (R)-1-(2-Bromo-phenyl)ethanamine | 200/202 |

PREPARATION 26

1-(2-Bromo-4-fluorophenyl)cyclobutanecarboxylic acid

Add potassium hydroxide (8.39 g, 150 mmol) and tetrabutylamine bromide (0.3 g, catalytic) to a solution of 2-(2-bromo-4-fluorophenyl)acetonitrile (4 g, 18.69 mmol) and 1,3-dibromopropane (4.15 g, 20.5 mmol) in toluene (20 mL). Stir it at 100° C. temperature for 2 h. Dilute the mixture with water and extract with ethyl acetate. Wash the organic layer with 1 N HCl and aqueous saturated sodium chloride. Dry over magnesium sulfate. Remove the organic solvent to give the crude product. Distill to give 1-(2-bromo-4-fluorophenyl)cyclobutanecarbonitrile (boiling point 110-120° C./0.3 Torr.) (1.5 g, 31%). MS (GC) m/z 253 [M]$^+$.

Add 6 mL of HCl saturated methanol to the above solid and stir overnight. Evaporate the solvent to dry. Add NaHCO$_3$ (1 M, 30 mL) and ether (20 mL). Stir for 15 min. Separate the organic layer and extract the aqueous layer with ether. Combine the ether solution and remove the solvent. Dissolve the residue in methanol (10 mL) and KOH (1.5 g) and stir over the weekend. Remove methanol and add water (30 mL). Extract with ethyl acetate and then acidify the aqueous layer with HCl. Extract the acidic solution with ethyl acetate, dry over MgSO$_4$, and remove the solvent to give the title compound (1.0 g, 24%). MS (ES) m/z 271 [M−1]$^−$.

PREPARATION 27

1-(2-Bromo-4-chlorophenyl)ethanamine

Stir a mixture of 1-(2-bromo-4-chlorophenyl)ethanol (2.33 g, 10 mmol), titanium isopropoxide (6 mL, 20 mmol) and ammonia in ethanol (25 mL, 50 mmol) under N$_2$ at ambient temperature for 6 h. Add sodium tetrahydroborate (0.6 g, 15 mmol) and stir the mixture for 3 h. Quench the reaction with ammonia hydroxide (2 N, 25 mL). Remove the insolubles by filtration. Extract the aqueous layer with ethyl acetate. Combine the organic layers and extract with an HCl solution (1 N, 30 mL). Wash the aqueous layer with ethyl acetate and then treat with a NaOH (2 N) solution to pH 10-12. Extract the aqueous layer with ethyl acetate (50 mL×3). Combine the organic layers and wash with aqueous saturated sodium chloride. Dry over magnesium sulfate. Remove the organic solvent to give the title compound (1.5 g, 64%). MS (ES) m/z 236 [M+1]$^+$.

PREPARATION 28

2-(2-Bromo-4-fluorophenyl)cyclopentanone

Heat a mixture of 2-bromo-4-fluoro-1-iodobenzene (4.5 g, 15 mmol), cyclopentanone (2.65 mL, 29.9 mmol), cesium carbonate (10.72 g, 32.9 mmol), 4,5-bis(disphenylphosphino)-9,9-dimethylxanthene (0.54 g, 0.9 mmol), and Palladium$_2$(dibenzalacetone)$_3$ [Pd$_2$(dba)$_3$)](0.35 g, 0.37 mmol) in dioxane (10 mL) to 80° C. under N$_2$ for 22 h. After cooling the mixture to RT, dilute with ether, filter through a celite pad, and remove the solvent. Purify the residue by column chromatography (hexane:ether/20:1) to give the title compound (0.55 g, 15%). MS (GC) m/z 258 [M]$^+$.

PREPARATION 29

1-(2-Bromo-4-fluorophenyl)-2,2-difluoroethanone

Add n-BuLi (8.86 mL, 14.18 mmol) slowly to a solution of 2-bromo-4-fluoro-1-iodobenzene (4.27 g, 14.2 mmol) in THF (50 mL) at −100° C. over 15 min under N$_2$. Stir the solution for 30 min. Add ethyl difluoroacetate (2.81 mL, 26.9 mmol) and stir for 3 h. Add an HCl (50 mL, 2 N) solution and warm the solution up to RT. Separate the organic layer, dry the organic layer over magnesium sulfate, and remove the solvent. Purify the residue by column chromatography (hexane:ethyl acetate/10:1) to give the title compound (2.3 g, 64%). MS (GC) m/z 252 [M]$^+$.

PREPARATION 30

5-(2-Bromo-4-fluorophenyl)-3,4-dihydro-2H-pyrrole

Treat a solution of 1-vinylpyrrolidin-2-one (2 g, 8.58 mmol) in dry THF (30 mL) with lithium diisopropylamide (LDA) (13 mL, 31.45 mmol) at −20° C. under N$_2$ atmosphere and stir at the same temperature for 30 min. Then add methyl 2-bromo-4-fluorobenzoate (2 g, 8.58 mmol) and stir it over the weekend. Add an HCl (12 N, 9 mL) solution and water (12 mL). Remove the THF and add HCl (12 N, 12 mL) and water (15 mL). Heat it to 100° C. for 15 h. Cool the mixture to RT and add a 5% NaOH solution. Extract the solution with ether, dry over magnesium sulfate, and remove the solvent. Purify the residue by column chromatography (hexane to ethyl acetate) to give the title compound (0.42 g, 27%). MS (ES) m/z 244 [M+1]$^+$.

PREPARATION 31

2-(2-Bromo-4-fluorophenyl)pyrrolidine

Add sodium tetrahydroborate (146 mg, 3.7 mmol) to a solution of 5-(2-bromo-4-fluorophenyl)-3,4-dihydro-2H-pyrrole (420 mg, 1.73 mmol) in methanol-acetic acid (saturated; 10 mL) mixture at −40° C. After warming up to RT, add water (10 mL) and make the solution basic with a NaOH solution (2 N). Extract the solution with DCM, wash the organic solution with aqueous saturated sodium chloride, dry over potassium carbonate, and remove the organic solvent to give the title compound (300 mg, 71%). MS (ES) m/z 236 [M+1]$^+$.

PREPARATION 32 tert-Butyl 1-(2-bromo-4-fluorophenyl)cyclobutylcarbamate

Add triethylamine (0.52 g, 5.13 mmol) and azidodiphenylphosphine (1.11 g, 4.03 mmol) to a solution of 1-(2-bromo-4-fluorophenyl)cyclobutanecarboxylic acid (1.0 g, 3.65 mmol) in tert-butanol (7.3 mL) at RT. Stir it at 50° C. for 30 min and at 90° C. overnight. Dilute the mixture with ether and wash the organic layer with saturated sodium bicarbonate, and aqueous saturated sodium chloride. Separate the organic layer and dry over magnesium sulfate. Filter and concentrate in vacuo to give a residue. Purify the residue by column chromatography [hexane:ether/20:1] to give the title compound (1.26 g, 48%). MS (ES) m/z 368 [M+23]$^+$.

PREPARATION 33

2-(2-Bromo-4-fluoro-phenyl)-acetamide

Combine (2-bromo-4-fluoro-phenyl)-acetyl chloride (3.5 g, 14 mmol), ammonium hydroxide (8.8 M in water, 50 mL, 0.45 mmol) and THF (10 mL) in a pressure vessel. Seal the vessel and stir the mixture overnight at RT. Dilute the mixture with chloroform-IPA (3:1, 100 mL). Wash the organic phase with aqueous saturated sodium chloride and water. Dry the mixture over sodium sulfate. Concentrate the solution in vacuo to give the title compound as a white solid (3.0 g, 93%). MS (ES) m/z 232/234 [M+1]$^+$.

PREPARATION 34

1-(2-Bromo-4-fluorophenyl)propan-1-amine

Stir a solution of triphenylphosphine (2.48 g, 9.44 mmol) and iodine (2.40 g, 9.44 mmol) for 10 min at RT. Add 1H-imidazole (0.97 g, 14.2 mmol) and stir for 10 min at RT. Add 1-(2-bromo-4-fluorophenyl)propan-1-ol (1.1 g, 4.72 mmol) and stir for 2 h at RT. Add a suspension of sodium azide (0.62 g, 9.44 mmol) in DMF (5 mL) and stir overnight. Dilute with DCM, and wash with water and aqueous saturated sodium chloride. Dry over sodium sulfate. Concentrate the solution in vacuo to a yellow oil.

Add a mixture of hydrazine (0.57 mL, 17.4 mmol) and formic acid (0.69 mL, 17.4 mmol) to a solution of the above yellow oil (0.9 g, 3.49 mmol) in ethanol (5 mL). Add Raney nickel (1.02 g, 17.4 mmol) slowly at 0° C. Stir the mixture for 5 h at RT. Filter to remove the excess nickel. Dilute the liquid with water and extract with chloroform. Dry the organic layer over sodium sulfate. Concentrate the solution in vacuo to a light yellow oil. Purify by column chromatography (DCM to 10% methanol in DCM) to give the title compound as a colorless oil (0.7 g, 87%). MS (ES) m/z 233 [M+1]$^+$.

PREPARATION 35

(2-Bromo-4-fluoro-phenyl)-N-(2-hydroxyethyl)-acetamide

Add thionyl chloride (1.5 g, 12.6 mmol) to a solution of (2-bromo-4-fluoro-phenyl)-acetic acid (0.3 g, 1.26 mmol) in DCM (3 mL). Reflux the mixture for 2 h. Remove the solvent and excess thionyl chloride under reduced pressure to give the intermediate (2-bromo-4-fluorophenyl)-acetyl chloride. Dissolve the residue in DCM (3 mL) and add to a stirred solution of ethanolamine (0.15 mL, 2.52 mmol) in DCM (3 mL) at 0° C. Stir the mixture overnight. Dilute with DCM and wash with saturated NaHCO$_3$, water, and aqueous saturated sodium chloride. Dry over sodium sulfate. Concentrate the solution in vacuo to give the title compound as a white solid (300 mg, 86%). MS (ES) m/z 276 [M+1]$^+$.

PREPARATION 36

2-Amino-1-(2-bromo-4-fluorophenyl)ethanol

Add trimethylsilyl cyanide (1.01 mL, 7.39 mmol) and zinc diiodide (0.11 g, 0.37 mmol) to a solution of 2-bromo-4-fluorobenzaldehyde (1.5 g, 7.39 mmol) in DCM (10 mL). Stir the mixture overnight at RT. Remove the solvent. Dissolve the residue in THF (5 mL) and cool at 0° C. Add borane-THF complex (11.1 mL, 11.1 mmol). Stir the mixture at RT for 3 h. Add 1 M HCl slowly and stir for 15 min. Adjust the pH to basic with saturated sodium carbonate. Extract with DCM. Dry it over sodium sulfate and concentrate to give the title compound as a colorless oil (1.5 g, 86%). MS (ES) m/z 235 [M+1]$^+$.

PREPARATION 37

1-(2-Bromo-4-fluorophenyl)cyclopropanamine

Add ethylmagnesium bromide (3 N, 53.9 mL, 74.9 mmol) to a solution of 2-bromo-4-fluorobenzonitrile(15 g, 73.5 mmol) and tetraisopropoxytitanium (23 mL, 162 mmol) in ether (25 mL) at −70° C. under N$_2$. After stirring at the temperature for 10 min, let it warm-up to RT and stir for one hour. Add boron trifluoride etherate (BF$_3$OEt$_2$) (16.8 mL, 147 mmol) to the solution slowly and stir for another hour. After adding 1 N HCl (200 mL) and ether (150 mL), separate the ether layer. Add 10% NaOH (150 mL) to the aqueous solution and extract it with ether. Separate the organic layer and dry over magnesium sulfate. Filter and concentrate in vacuo to give a residue. Purify the residue by column chromatography (diethylether) to give the title compound (7.5 g, 44%). MS (ES) m/z 230 [M+1]$^+$.

PREPARATION 38 tert-Butyl 1-(2-bromo-4-fluorophenyl)cyclopropylcarbamate

Add NaOH (0.78 g, 19.5 mmol) and di-tert-butyl dicarbonate [(Boc)$_2$O] (4.2 g, 19.1 mmol) to a solution of 1-(2-bromo-4-fluorophenyl)cyclopropylamine (3.5 g, 15.2 mmol) in tert-butanol (18 mL) and water (26 mL). After stirring for one hour at RT, extract the reaction mixture with ether. Separate the organic layer and dry it over magnesium sulfate. Filter and concentrate in vacuo. Purify the residue by column chromatography (hexane/diethylether) to give the title compound (4.45 g, 89%). $^1$H NMR (400 MHz-CDCl$_3$) δ 7.61 (bs, 1H), 7.25 (dd, J=7.6, 4 Hz, 1H), 6.95 (t d, J=8.4, 2.4 Hz, 1H), 5.547 (s, 1H), 1.372 (s, 9H), 1.1 (m, 2H), 0.881 (m, 2H).

Prepare the following intermediates with procedures similar to those described above:

| Prep | Compound Name | MS (ES) m/z [M + 1]$^+$ |
|---|---|---|
| 39 | tert-Butyl 1-(2-bromo-4-chlorophenyl)ethylcarbamate | 346 |
| 40 | tert-Butyl 2-(2-bromo-4-fluorophenyl)pyrrolidine-1-carboxylate | 344 |
| 41 | tert-Butyl 2-(2-bromo-4-fluorophenyl)-2-fluoropropylcarbamate | 351 |

PREPARATION 42

[1-(2-Bromo-phenyl)-ethyl]-carbamic acid tert-butyl ester

Add diisopropylethylamine (1.5 g, 12 mmol) to a solution of 1-(2-bromo-4-fluoro-phenyl)-ethylamine (4 g, 20 mmol) and di-tert-butyldicarbonate (6.5 g, 30 mmol) in 20 mL of DCM. Stir the mixture overnight at RT. Dilute the mixture with chloroform/IPA (3/1), wash with aqueous saturated sodium chloride and water, dry it over sodium sulfate and concentrate in vacuo. Purify the crude product by column chromatography (10% methanol in DCM) to give the title compound (2.0 g, 33%). MS (ES) m/z 244/246 [M-tert-butyl]$^+$.

Prepare the following intermediates with procedures similar to those described above:

| Prep | Compound Name | MS (ES) m/z [M-tert-butyl]+ |
|---|---|---|
| 43 | [1-(2-Bromo-4-fluoro-phenyl)-ethyl]-carbamic acid tert-butyl ester | 244/246 |
| 44 | [2-(2-Bromo-4-fluoro-phenyl)-ethyl]-carbamic acid tert-butyl ester | 262/264 |
| 45 | [2-(2-Bromo-phenyl)-ethyl]-carbamic acid tert-butyl ester | 244/246 |
| 46 | 2-(2-Bromo-4-fruorophenyl)propan-2-yl tert-butyl carbonate | 346/348 |
| 47 | (R)-tert-Butyl 1-(2-bromophenyl)ethylcarbamate | 300/302 |
| 48 | tert-Butyl 1-(2-bromo-4-fluorophenyl)-2,2,2-trifluoroethylcarbamate | 372/374 |
| 49 | tert-Butyl 2-(2-bromo-4-fluorophenyl)-2-hydroxyethylcarbamate | 357/359 [M + Na]+ |
| 50 | tert-Butyl 1-(2-bromo-4-fluorophenyl)propylcarbamate | 332/334 |

PREPARATION 51

(R)-tert-Butyl 1-(2-bromo-4-fluorophenyl)ethylcarbamate

Separate (R)-tert-butyl 1-(2-bromo-4-fluorophenyl)ethylcarbamate by chiral chromatography (Chiralcel® OD-H Column: 40% methanol, 0.2% isopropyl amine in $CO_2$; flow rate, 5 mL/min; detection, 225 nm) to give the title compound. MS (ES) m/z 478 [M+1]+. Determine chirality by Vibration Circular Dichroic (VCD) spectroscopy.

PREPARATION 52 tert-Butyl 1-(2-bromo-4-fluorophenyl)ethyl(methyl)carbamate

Add sodium hydride (0.89 g, 22.4 mmol, 60% dispersion in mineral oil) to a solution of tert-butyl 1-(2-bromo-4-fluorophenyl)ethylcarbamate (4.75 g, 14.9 mmol) in DMF (10 mL). Stir the mixture for 30 min at RT. Add methyl iodide (1.86 mL, 29.9 mmol). Stir the mixture for 1 h at RT. Dilute with ethyl acetate, and wash with water and aqueous saturated sodium chloride. Dry over sodium sulfate and concentrate. Purify by column chromatography (hexane to 20% ethyl acetate in hexane) to give the title compound as a colorless oil (4.9 g, 98%). $^1$H NMR (400 MHz, $CD_3Cl$) δ 1.32 (s, 9H), 1.45 (t, J=8.0 Hz, 3H), 2.58 (s, 3H), 5.39 (br, 1H), 7.00 (m, 1H), 7.28 (m, 2H).

Prepare the following intermediate with a procedure similar to the one described above:

| Prep | Compound Name | MS (ES) m/z [M-t-butyl]+ |
|---|---|---|
| 53 | tert-Butyl 1-(2-bromo-4-fluorophenyl)cyclopropyl(methyl)carbamate | 288/290 |

PREPARATION 54 tert-Butyl 2-(2-bromo-4-fluorophenyl)aziridine-1-carboxylate

Add potassium hydroxide (1.15 g, 17.5 mmol, fresh powder) to a solution of tert-butyl 2-(2-bromo-4-fluorophenyl)-2-hydroxyethylcarbamate (1.19 g, 3.56 mmol) and p-toluenesulfonyl chloride (0.75 g, 3.88 mmol) in dry THF (50 mL). Stir the mixture overnight at RT. Dilute with DCM, and wash with water and aqueous saturated sodium chloride. Dry over sodium sulfate and concentrate. Purify by column chromatography (hexane to 5% ethyl acetate in hexane) to give the title compound as a colorless oil (0.46 g, 41%). $^1$H NMR (400 MHz, $CD_3Cl$) δ 1.47 (s, 9H), 2.08 (d, J=3.2 Hz, 1H), 2.67 (d, J=5.6 Hz, 1H), 3.59 (dd, J=3.6 Hz, 6.0 Hz, 1H), 7.00 (m, 1H), 7.28 (m, 1H), 7.35 (m, 1H).

PREPARATION 55

1-(2-Bromo-4-fluoro-phenyl)-3-[1,3]dioxan-2-yl-propan-1-ol

Add (1,3-dioxan-2-ylethyl)magnesium bromide (0.5 M in THF, 40 mL, 20 mmol) to a solution of 2-bromo-4-fluorobenzaldehyde (3 g, 15 mmol) in THF (20 mL) at 0° C. under $N_2$. Continue to stir the mixture for 48 h at RT. Quench the reaction mixture with 1 N HCl, followed by the basification with diluted ammonium hydroxide to ~pH 9. Extract the product with chloroform/IPA (3/1). Dry the organic layer over sodium sulfate. Concentrate the solution in vacuo. Purify by column chromatography (10% methanol in DCM) to give the title compound as a yellow oil (24.5 g, 95%). MS (ES) m/z 319/321 [M+1]+.

PREPARATION 56

1-(2-Bromo-4-fluoro-phenyl)-butane-1,4-diol

Heat a mixture of 1-(2-bromo-4-fluoro-phenyl)-3-[1,3]dioxan-2-yl-propan-1-ol (4.0 g, 12.5 mmol) and acetic acid (20 mL, 280 mmol) at 100° C. for 30 min. Dilute the reaction mixture with sodium carbonate (2 N). Extract the product into chloroform. Dry the organic phase over sodium sulfate. Concentrate the solution in vacuo to a give the intermediate aldehyde. To the solution of the above intermediate in methanol (50 mL), add sodium borohydride (1.42 g, 37.6 mmol). Stir the mixture at RT for 1 h. Quench the reaction with diluted HCl. Extract the product into chloroform. Dry the organic phase over sodium sulfate. Concentrate the solution in vacuo to a give the title compound as a yellow oil (2.5 g, 76%). MS (ES) m/z 288 [M+Na]+.

PREPARATION 57

2-(2-Bromo-4-fluoro-phenyl)-tetrahydro-furan

Combine 1-(2-bromo-4-fluoro-phenyl)-butane-1,4-diol (1 g, 3.8 mmol), silver (I)hexafluoroantimonate (131 mg, 0.4 mmol), platinum(II) chloride (40 mg, 0.2 mmol) in 1,2-dichloroethane (10 mL) in a pressure tube. Seal the tube and heat the mixture overnight at 110° C. Dilute the mixture with chloroform-IPA (3:1, 100 mL). Wash the organic phase with aqueous saturated sodium chloride and water. Dry the mixture over sodium sulfate. Concentrate the solution in vacuo. Purify by column chromatography (20% ethyl acetate in hexane) to give the title compound as a pale yellow oil (0.72 g, 77%).

PREPARATION 58

2-[2-(2-Bromo-phenoxy)-ethoxy]-tetrahydropyran

Add 2-bromo-phenol (10 g, 57.80 mmol) to a suspension of sodium hydride (60% dispersion in mineral oil, 2.77 g, 69.36 mmol) in DMF (6 mL). Stir the mixture for 1 h. Add 2-(2-bromo-ethoxy)-tetrahydropyran (13.54 g, 64.74 mmol). Stir the solution at RT overnight. Dilute the mixture with ethyl acetate and water. Wash the organic layer with aqueous saturated sodium chloride and water. Dry the mixture over sodium sulfate. Concentrate the solution in vacuo. Purify by column chromatography (10% ethyl acetate in hexane) to give the title compound (13.9 g, 80%) as a light yellow oil. MS (ES) m/z 323 [M+Na]$^+$.

PREPARATION 59

[2-(2-Bromo-phenyl)-ethyl]-carbamic acid tert-butyl ester

Add di-tert-butyldicarbonate (2.7 g, 12.4 mmol) to a solution of 2-bromophen-ethylamine (1.65 g, 8.25 mmol), triethylamine (3.45 mL, 24.7 mmol) and 4-dimethylaminopyridine (DMAP) (100 mg) in DCM (16.5 mL) and stir at RT overnight. Dilute with DCM, wash with saturated NaHCO$_3$ followed by saturated NH$_4$Cl, dry organics with Na$_2$SO$_4$, filter, concentrate, and purify by filtering through a pad of silica and eluting with 1:1 ethyl acetate: hexanes to give the title compound. MS (ES) m/z 244 [M-tert-Butyl]$^-$.

PREPARATION 60

{2-[2-(4,4,5,5-Tetramethyl-[1,3,2]dioxaborolan-2-yl)-phenyl]-ethyl}-carbamic acid tert-butyl ester Add Pd(dppf)Cl$_2$ (71 mg, 84.9 µmol) to a suspension of [2-(2-bromo-phenyl)-ethyl]-carbamic acid tert-butyl ester (0.85 g, 2.83 mmol), bis(pinacolato)diboron (810 mg, 3.11 mmol), and potassium acetate (830 mg, 8.49 mmol) in 1,4-dioxane (11.3 mL) and heat at 100° C. for 5 h. Cool to RT and concentrate. Dissolve the residue in DCM and filter through a pad of silica (1 cm pad in 30-mL sintered glass funnel) washing with 20 mL of DCM. Concentrate to give the title compound. MS (ES) m/z 248 [M-Boc]$^+$.

PREPARATION 61

1-(2-Bromo-4-fluoro-phenoxy)propan-2-one

Cool a suspension of 2-bromo-4-fluoro-phenol (1 g, 4.89 mmol) and K$_2$CO$_3$ (1.8 g, 13.2 mmol) in DMF (10 mL) to 0° C. in an ice bath under nitrogen. Add chloroacetone (678 mg, 7.33 mmol) during a period of 30 min. Stir the mixture at RT overnight. Add water and extract with ethyl acetate. Wash the solution with aqueous saturated sodium chloride. Dry over sodium sulfate. Concentrate the solution in vacuo. Purify by column chromatography (hexane to 10% ethyl acetate in hexane) to give the title compound as a yellow oil (0.75 g, 59%). $^1$H NMR (400 MHz-CDCl$_3$) δ 2.35 (s, 3H), 4.51 (s, 2H), 6.73 (dd, J=4.8, 8.8 Hz, 1H), 6.97 (m, 1H), 7.32 (m, 1H).

PREPARATION 62

1-(2-Bromo-4-fluoro-phenoxy)-2-methyl-propan-2-ol

Cool a solution of 1-(2-bromo-4-fluoro-phenoxy)-propan-2-one (520 mg, 2.10 mmol) in THF (4 mL) to 0° C. in an ice bath under nitrogen. Add methylmagnesium chloride (3.0 M in THF, 0.84 mL, 2.53 mmol) dropwise. Stir the mixture at 0° C. for an additional half an hour. Add water and extract with ethyl acetate. Wash the solution with aqueous saturated sodium chloride. Dry over sodium sulfate. Concentrate the solution in vacuo. Purify by column chromatography (hexane to 30% ethyl acetate in hexane) to give the title compound as a yellow oil (230 mg, 42%). MS (ES) m/z 285 [M+Na]$^+$.

PREPARATION 63

2-Bromo-1-bromomethyl-4-fluoro-benzene

Combine 2-bromo-4-fluoro-1-methyl-benzene (15 g, 79.3 mmol), N-bromosuccinimide (18.08 g, 101.6 mmol), and 2,2-azobisisobutyronitrile (3.9 g, 23.8 mmol) in carbon tetrachloride (150 mL) in a round bottom flask fitted with a reflux condensor. Heat the mixture at reflux for 21 h. Cool the mixture and remove the solvent under reduced pressure. Suspend the crude mixture in DCM and wash with water. Wash the organics with aqueous saturated sodium chloride and dry over sodium sulfate. Filter and remove the solvent under reduced pressure to obtain the crude product. Purify by column chromatography (1% ethyl acetate in hexane→10% ethyl acetate in hexanes) to give the title compound as an oily white solid (18.5 g, 87%). GCMS m/z 268 [M]$^+$.

PREPARATION 64

4-(2-Bromo-4-fluoro-benzyl)-morpholine

Combine 2-bromo-1-bromomethyl-4-fluoro-benzene (4 g, 14.9 mmol), morpholine (2.6 mL, 29.8 mmol), and diisopropylethylamine (5.2 mL, 29.8 mmol) in acetonitrile (10.0 mL). Heat the reaction mixture at 81° C. for 2 h and cool to RT. Remove the solvent under reduced pressure. Dilute with DCM and wash with water and then aqueous saturated sodium chloride. Dry the organics over sodium sulfate. Filter and remove the solvent under reduced pressure to obtain the title compound (3.9 g, 95%). LCMS (ES) m/z 274 [M+1]$^+$.

PREPARATION 65

(2-Bromo-4-fluorobenzyl)-dimethyl-amine

Combine 2-bromo-4-fluorobenzaldehyde (5 g, 24.63 mmol), dimethylamine (2 M, 49.26 mL, 98.52 mmol) and acetic acid (8.47 mL, 147.78 mmol) in DCM (50 mL), and stir for 30 min. To this mixture, add sodium triacetoxyborohydride (49.26 mmol, 10.44 g) and stir overnight at RT. Wash with saturated NaHCO$_3$ solution (100 mL), dry with aqueous saturated sodium chloride, and then dry over sodium sulfate. Filter the organics and remove the solvent under reduced pressure to give the title compound as a brownish oil (4.56 g). GCMS m/z 232 [M]$^+$.

Prepare the following intermediates with procedures similar to those described above:

| Prep | Compound Name | LCMS (ES) m/z [M + 1]$^+$ | Comments |
|---|---|---|---|
| 66 | 2-[(2-Bromo-4-fluoro-benzyl)-methyl-amino]-ethanol | | 1H NMR (400 MHz-CD$_3$OD$_3$) δ 2.24 (s, 3H), 2.59 (t, J = 6.0 Hz, 2H), 3.61 (s, 2H), 3.66 (t, J = 6.0 Hz, 2H), 4.85 (s, 1H), 7.07 (m, 1H), 7.32 (dd, J = 2.0, |

-continued

| Prep | Compound Name | LCMS (ES) m/z [M + 1]+ | Comments |
|---|---|---|---|
| 67 | 1-(2-Bromo-4-fluoro-benzyl)-piperidin-4-ol | 288 | 8.4 Hz, 1H), 7.52 (dd, J = 2.0, 8.4 Hz, 1H). |

PREPARATION 68

N-(1-(2-Bromo-4-fluorophenyl)ethyl)-2,2-difluoro-acetamide

Add difluoroacetic acid (777 mg, 8.1 mmol) to a mixture of 1-(2-bromo-4-fluorophenyl)ethanamine (1.18 g, 5.4 mmol), 1-(3-dimethylaminopropyl)-3-ethylcarbodiimide hydrochloride (1.55 g, 8.1 mmol), 1-hydroxybenzotriazole hydrate (1.24 g, 8.1 mmol), and triethylamine (2.26 mL, 16.2 mmol) in DCM (20 mL) at 0° C. Stir the mixture at RT overnight. Dilute the mixture with DCM, wash with water and aqueous saturated sodium chloride. Separate the organic layer and dry over sodium sulfate. Filter and concentrate in vacuo. Purify the residue by column chromatography [5% to 50% ethyl acetate in hexanes] to give the title compound (1.06 g, 44%). MS (ES) m/z 296 [M+1]+.

PREPARATION 69

N-(1-(2-Bromo-4-fluorophenyl)ethyl)-2,2-difluoroethanamine

Add borane-THF complex (10.69 mL, 10.7 mmol) to a solution of N-(1-(2-bromo-4-fluorophenyl)ethyl)-2,2-difluoroacetamide (1.06 g, 3.56 mmol) in THF (3 mL). Reflux the mixture for 17 h. Quench with hydrochloric acid (5 N, 8 mL). Stir the solution for 1 h. Add saturated NaHCO$_3$. Dilute the mixture with DCM, wash with water and aqueous saturated sodium chloride. Separate the organic layer and dry over sodium sulfate. Filter and concentrate in vacuo to give the title compound (0.94 g, 93%). MS (ES) m/z 282 [M+1]+.

PREPARATION 70

2-Benzo[b]thiophen-7-yl-4-fluoro-phenol

Combine 7-bromo-benzo[b]thiophene (6.53 g, 30.64 mmol), 5-fluoro-2-hydroxy phenyl boronic acid (4.87 g, 31.26 mmol), Pd(dppf)Cl$_2$ (1.25 g, 1.53 mmol), 2-(di-tert-butylphosphino)biphenyl (0.28 g, 0.92 mmol), sodium carbonate (2 M, 30.64 mL, 61.92 mmol) in dioxane (60 mL, alternative THF) in a flask. Heat the mixture at 100° C. for 2 h. Dilute the mixture with chloroform/IPA (3/1). Wash the solution with aqueous saturated sodium chloride. Dry over sodium sulfate. Concentrate the solution in vacuo. Purify the residue by column chromatography (hexane to 10% ethyl acetate in hexane) to give the title compound (6.0 g, 80%) as a yellow solid. MS (ES) m/z 243 [M−1]+.

Prepare the following intermediates with procedures similar to those described above:

| Prep | Compound Name | MS (ES) m/z [M + 1]+ | Comments |
|---|---|---|---|
| 71 | 2-Benzo[b]thiophen-7-yl-phenol | 227 | |
| 72 | 2-(2-Benzo[b]thiophen-7-yl-4-fluoro-phenyl)-tetrahydro-furan | Two atropisomers | $^1$H NMR (CD$_2$Cl$_2$) δ 7.82 (1H), 7.67 (1H), 7.74 (3H), 7.19 (2H), 7.07 (1H), 4.79 (0.5 H), 4.55 (0.5 H), 4.05 (1H), 3.71 (1H), 1.95 (1H), 1.66 (1H). |
| 73 | [2-(2-Benzo[b]thiophen-7-yl-4-fluoro-phenyl)-ethyl]-carbamic acid tert-butyl ester | 394 | Observed at [M + Na]+ |
| 74 | [1-(2-Benzo[b]thiophen-7-yl-phenyl)-ethyl]-carbamic acid tert-butyl ester | 376 | Observed at [M + Na]+ |
| 75 | 4-(2-Benzo[b]thiophen-7-yl-4-fluoro-benzyl)-morpholine | 328 | |
| 76 | (2-Benzo[b]thiophen-7-yl-4-fluoro-benzyl)-dimethyl-amine | 286 | 2-(di-tert-butyl-phosphino)biphenyl used with Pd(dppf)Cl$_2$ |
| 77 | 2-[2-(2-Benzo[b]thiophen-7-yl-4-fluoro-phenoxy)-ethoxy]-tetrahydropyran | 395 | Observed at [M + Na]+ |
| 78 | 2-[2-(2-Benzo[b]thiophen-7-yl-phenoxy)-ethoxy]-tetrahydropyran | 377 | Observed at [M + Na]+ |
| 79 | 7-(5-Fluoro-2-methyl-phenyl)-benzo[b]thiophene | 242 | GCMS used to analyze [M]+ |
| 80 | 7-(2-Chloro-5-fluoro-phenyl)-benzo[b]thiophene | 262 | GCMS used to analyze [M]+ |
| 81 | (R)-tert-Butyl 1-(2-(benzo[b]thiophen-7-yl)-4-fluorophenyl)ethylcarbamate | 372 | |

PREPARATION 82

[2-(2-Benzo[b]thiophen-7-yl-phenoxy)-ethyl]-carbamic acid tert-butyl ester

Add sodium hydride (424 mg, 18 mmol) to a solution of 2-benzo[b]thiophen-7-yl-phenol (1 g, 4.4 mmol) in 10 mL of DMF. Stir the mixture at RT for 1 h and add (2-bromo-ethyl)-carbamic acid tert-butyl ester (2 g, 8.9 mmol). Continue to stir the reaction mixture for another 4 h at RT. Dilute the mixture with chloroform-IPA (3:1, 100 mL). Wash the organic phase with aqueous saturated sodium chloride and water. Dry the mixture over sodium sulfate. Concentrate the solution in vacuo. Purify the residue by column chromatography (20% ethyl acetate in hexane) to give the title compound as a pale yellow solid (1.4 g, 86%). MS (ES) m/z 392 [M+Na]+.

Prepare the following intermediate by a procedure similar to the one described above:

| Prep | Compound Name | MS (ES) m/z [M + Na]+ |
|---|---|---|
| 83 | [2-(2-Benzo[b]thiophen-7-yl-4-fluoro-phenoxy)-ethyl]-carbamic acid tert-butyl ester | 410 |

PREPARATION 84

[2-(2-Benzo[b]thiophen-7-yl-4-fluoro-phenoxy)-ethyl]-methyl-carbamic acid tert-butyl ester Add sodium hydride (620 mg, 26 mmol) to a solution of 2-benzo[b]thiophen-7-yl-4-fluoro-phenol (1 g, 2.6 mmol) in 15 mL of DMF. Stir the mixture at RT for 1 h and add methyl iodide (3.7 g, 26 mmol). Continue to stir the reaction mixture for another 4 h at RT. Dilute the mixture with chloroform-IPA (3:1, 100 mL). Wash the organic phase with aqueous saturated sodium chloride and water. Dry the mixture over sodium sulfate. Concentrate the solution in vacuo to a yellow oil. Purify the residue by column chromatography (20% ethyl acetate in hexane) to give the title compound as a pale yellow solid (0.85 g, 82%). MS (ES) m/z 424 [M+Na]$^+$.

Prepare the following intermediates by a procedure similar to the one described above:

| Prep | Compound Name | MS (ES) m/z [M + Na]$^+$ | Comments |
|---|---|---|---|
| 85 | [[2-(2-Benzo[b]thiophen-7-yl-4-fluoro-phenyl)-ethyl]-methyl-carbamic acid tert-butyl ester | 408 | |
| 86 | [2-(2-Benzo[b]thiophen-7-yl-phenyl)-ethyl]-methyl-carbamic acid tert-butyl ester | 312 | Observed at [M-tert-Butyl] |
| 87 | tert-Butyl 1-(2-bromo-4-fluorophenyl)-2,2,2-trifluoroethyl(methyl)carbamate | 386/388 | |
| 88 | tert-Butyl 1-(2-bromo-4-fluorophenyl)ethyl(methyl)carbamate | 332/334 | |

PREPARATION 89

2-Chloro-5-fluoro-4-(7-{2-[2-(tetrahydro-pyran-2-yloxy)-ethoxy]-phenyl}-benzo[b]thiophen-2-yl)-pyrimidine In a 500-mL round bottom flask, cool a solution of 2-[2-(2-benzo[b]thiophen-7-yl-phenoxy)-ethoxy]-tetrahydropyran (500 mg, 1.41 mmol) and triisopropylborate (530 mg, 2.82 mmol) in THF (30 mL) to −70° C. under N$_2$. To the solution, add lithium diisopropylamide (2 M in THF, 1.41 mL, 2.82 mmol) gradually over a period of 30 min. Stir the mixture continually for an additional 1 h in the cooling bath. Gradually transfer the mixture into a refluxing solution of 2,4-dichloro-5-fluoropyrimidine (353 mg, 2.12 mmol), Pd(dppf)Cl$_2$ (57.6 g, 0.07 mmol) and sodium carbonate (2 M in water, 1.8 mL, 3.6 mmol) in THF (20 mL) over a period of 30 min. Reflux for an additional 1 h. Cool the mixture to RT and dilute with chloroform/IPA (3/1) and water. Wash the organic layer with aqueous saturated sodium chloride. Dry over sodium sulfate. Concentrate in vacuo. Purify the residue by FCC (20% ethyl acetate in hexane) to give the title compound (550 mg, 80%). MS (ES) m/z 507 [M+Na]$^+$.

Prepare the following intermediates with essentially those procedures used for 2-Chloro-5-fluoro-4-(7-{2-[2-(tetrahydro-pyran-2-yloxy)-ethoxy]-phenyl}-benzo[b]thiophen-2-yl)-pyrimidine using the appropriate starting material:

| Prep | Compound Name | MS (ES) m/z [M + 1]$^+$ | Comments |
|---|---|---|---|
| 90 | 2-Chloro-5-fluoro-4-(7-{5-fluoro-2-[2-(tetrahydro-pyran-2-yloxy)-ethoxy]-phenyl}-benzo[b]thiophen-2-yl)-pyrimidine | 525 | Observed at [M + Na]$^+$ |
| 91 | 2-Chloro-4-[7-(5-fluoro-2-methyl-phenyl)-benzo[b]thiophen-2-yl]-pyrimidine | 355 | |
| 92 | 2-Chloro-4-[7-(2-chloro-5-fluoro-phenyl)-benzo[b]thiophen-2-yl]-pyrimidine | 375 | |
| 93 | 4-{2-[2-(2-Chloro-5-fluoro-pyrimidin-4-yl)-benzo[b]thiophen-7-yl]-4-fluoro-benzyl}-morpholine | 458 | 2-(di-tert-butyl-phosphino)-biphenyl used with Pd(dppf)Cl$_2$ |
| 94 | {2-[2-(2-Chloro-5-fluoro-pyrimidin-4-yl)-benzo[b]thiophen-7-yl]-4-fluoro-benzyl}-dimethyl-amine | 416 | Same as Prep 94 |
| 95 | 2-Chloro-5-fluoro-4-{7-[5-fluoro-2-(tetrahydro-furan-2-yl)-phenyl]-benzo[b]thiophen-2-yl}-pyrimidine | 429 | |
| 96 | ((2-{2-[2-(2-Chloro-5-fluoro-pyrimidin-4-yl)-benzo[b]thiophen-7-yl]-phenoxy}-ethyl)-carbamic acid tert-butyl ester | 522 | Observed at [M + Na]$^+$ |
| 97 | (2-{2-[2-(2-Chloro-5-fluoro-pyrimidin-4-yl)-benzo[b]thiophen-7-yl]-4-fluoro-phenoxy}-ethyl)-carbamic acid tert-butyl ester | 540 | Observed at [M + Na]$^+$ |
| 98 | (2-{2-[2-(2-Chloro-5-fluoro-pyrimidin-4-yl)-benzo[b]thiophen-7-yl]-4-fluoro-phenyl}-ethyl)-methyl-carbamic acid tert-butyl ester | 538 | Observed at [M + Na]$^+$ |
| 99 | (2-{2-[2-(2-Chloro-5-fluoro-pyrimidin-4-yl)-benzo[b]thiophen-7-yl]-phenyl}-ethyl)-methyl-carbamic acid tert-butyl ester | 520 | Observed at [M + Na]$^+$ |
| 100 | 4-(7-Bromo-benzo[b]thiophen-2-yl)-2-fchloro-5-luoro-pyrimidine | 476 | |
| 101 | 4-(7-Bromobenzo[b]thiophen-2-yl)-2,5-dichloropyrimidine | 359 | |
| 102 | 4-(7-Bromobenzo[b]thiophen-2-yl)-2-chloro-5-methylpyrimidine | 339 | |
| 103 | 4-(7-Bromobenzo[b]thiophen-2-yl)-2-chloropyrimidine | 325 | |
| 104 | (R)-tert-Butyl 1-(2-(2-(2-chloro-5-fluoropyrimidin-4-yl)benzo[b]thiophen-7-yl)-4-fluorophenyl)ethylcarbamate | 502 | |

PREPARATION 105

2-(2-(5-(Hydroxymethyl)-1H-1,2,3-triazol-1-yl)ethyl)isoindoline-1,3-dione

Heat a mixture of 2-(2-azidoethyl)isoindoline-1,3-dione (12 g, 55.5 mmol) and 2-propyn-1-ol (3.88 mL, 66.6 mmol) in toluene (50 mL) in a sealed reactor at 90° C. for 3 days. Cool to RT and collect the solid. Purify by column chromatography (DCM to 2% methanol in DCM) to give the title compound (first fraction) as a white solid (4.7 g, 31%). MS (ES) m/z 273 [M+1]$^+$.

Isolate the following regioisomer from the second fraction of the above chromatography:

| Prep | Compound Name | MS (ES) m/z [M + 1]⁺ |
|---|---|---|
| 106 | 2-(2-(4-(Hydroxymethyl)-1H-1,2,3-triazol-1-yl) ethyl) isoindoline-1,3-dione | 273 |

PREPARATION 107

2-(2-(4-(Iodomethyl)-1H-1,2,3-triazol-1-yl)ethyl) isoindoline-1,3-dione

Stir a mixture of triphenylphosphine (0.29 g, 1.10 mmol) and iodine (0.28 g, 1.10 mmol) in DCM (4 mL) for 10 min. Add 1H-imidazole (0.12 g, 1.84 mmol) and stir for 10 min. Add 2-(2-(4-(hydroxymethyl)-1H-1,2,3-triazol-1-yl)ethyl) isoindoline-1,3-dione (0.2 g, 0.73 mmol) and stir overnight at RT. Dilute with DCM and wash with water and aqueous saturated sodium chloride. Dry over sodium sulfate. Concentrate the solution in vacuo. Purify by column chromatography (DCM to 20% ethyl acetate in DCM) to give the title compound as a yellow solid (0.22 g, 78%). MS (ES) m/z 383 [M+1]⁺.

Prepare the following intermediate with a procedure similar to the one described above:

| Prep | Compound Name | MS (ES) m/z [M + 1]⁺ |
|---|---|---|
| 108 | 2-(2-(5-(Iodomethyl)-1H-1,2,3-triazol-1-yl)ethyl)isoindoline-1,3-dione | 383 |

PREPARATION 109

2-(2-(4-Methyl-1H-1,2,3-triazol-1-yl)ethyl)isoindoline-1,3-dione

Stir a mixture of 2-(2-(4-(iodomethyl)-1H-1,2,3-triazol-1-yl)ethyl)isoindoline-1,3-dione (1 g, 2.62 mmol) and 0.2 g of 10% palladium on carbon in ethanol (10 mL) under hydrogen balloon overnight. Filter to remove the solid and concentrate. Purify by column chromatography (DCM to 20% ethyl acetate in DCM) to give the title compound as a yellow solid (0.5 g, 74%). MS (ES) m/z 257 [M+1]⁺.

Prepare the following intermediate with procedures similar to those described for 2-(2-(4-Methyl-1H-1,2,3-triazol-1-yl) ethyl)isoindoline-1,3-dione:

| Prep | Compound Name | MS (ES) m/z [M + 1]⁺ |
|---|---|---|
| 110 | 2-(2-(5-Methyl-1H-1,2,3-triazol-1-yl)ethyl)isoindoline-1,3-dione | 257 |

PREPARATION 111

2-(2-[1,2,3]Triazol-1-yl-ethyl)-isoindole-1,3-dione

Add 1H-1,2,3-triazole (250 g; 3.51 mol), N-(2-bromoethyl)phthalimide (942 g; 3.52 mol) and 1500 mL of DMF to a 5-L roundbottom flask fitted with a mechanical stirrer, nitrogen inlet and temperature probe. Cool the mixture to 15° C. Stir the mixture until all of the solids are nearly dissolved and then cool in an ice-water bath. Add cesium carbonate (1145 g; 3.51 mol) in portions over 10 min. The reaction mixture exotherms to 21° C. Allow the mixture to stir and come to RT overnight. Pour the reaction mixture into a 12-L flask containing 8 L of ice-water. Stir the suspension for 30 min and then filter and rinse the solid with 3 L of water. Air-dry for 2 h. Recrystallize the mixture of regioisomers from 7 L of absolute ethanol. Isolate the solid by filtration and air-dry. Recrystallize again from 16 L of absolute ethanol. Isolate the solids by filtration and rinse with fresh ethanol (1000 mL). Vacuum-dry the solids at 40° C. to give the title compound, 292.7 g (34%) as a white solid. MS (EI) m/z 243 [M+1]⁺.

PREPARATION 112

2-[1,2,3]Triazol-1-yl-ethylamine

Dissolve 2-(2-[1,2,3]triazol-1-yl-ethyl)-isoindole-1,3-dione (106 g; 437.59 mmol) in a 5-L round bottom flask containing 2 L of absolute ethanol. Heat the stirred mixture to 70° C. under nitrogen; at this temperature add dropwise hydrazine monohydrate (23 mL; 463.76 mmol; 23.69 g) over 10 min. The mixture becomes homogeneous and yellow in color. After about 30 min at this temperature a solid begins to form in the reaction and the color gradually becomes much less yellow over time. After 7 h remove the heat and cool to RT over 1 h. Filter over diatomaceous earth and rinse with 1000 mL of ethanol. Evaporate to a semi-solid. Dissolve in 2 L of CH₂Cl₂, filter over diatomaceous earth and evaporate. Dilute the residue with toluene (1500 mL) and filter over diatomaceous earth to remove the insoluble tan solid. Evaporate and place under vacuum overnight. Dissolve the oil in 100 mL of CH₂Cl₂ and filter again through a pad of diatomaceous earth. Evaporate to 43.9 g (90%) of the title compound as a cloudy oil. MS (EI) m/z 112 [M]⁺.

Prepare the following intermediates with procedures similar to those used for 2-[1,2,3]Triazol-1-yl-ethylamine:

| Prep | Compound Name | MS (ES) m/z [M + 1]⁺ |
|---|---|---|
| 113 | (1-(2-Aminoethyl)-1H-1,2,3-triazol-5-yl)methanol | 143 |
| 114 | (1-(2-Aminoethyl)-1H-1,2,3-triazol-4-yl)methanol | 143 |
| 115 | 2-(4-Methyl-1H-1,2,3-triazol-1-yl)ethanamine | 127 |
| 116 | 2-(5-Methyl-1H-1,2,3-triazol-1-yl)ethanamine | 127 |

Prepare the following intermediates with procedures similar to those described for 2-(2-(2-(2-(1H-1,2,3-Triazol-1-yl)ethylamino)-5-fluoropyrimidin-4-yl)benzo[b]thiophen-7-yl)phenoxy)ethanol below:

| Prep | Compound Name | MS (ES) m/z [M + 1]+ | Comments |
|---|---|---|---|
| 117 | [4-(7-Bromo-benzo[b]thiophen-2-yl)-5-fluoro-pyrimidin-2-yl]-(2-[1,2,3]triazol-1-yl-ethyl)-amine | 419/421 | |
| 118 | N-(2-(1H-1,2,3-Triazol-1-yl)ethyl)-4-(7-bromobenzo[b]thiophen-2-yl)pyrimidin-2-amine | 401, 403 | |
| 119 | N-(2-(1H-1,2,3-Triazol-1-yl)ethyl)-4-(7-bromobenzo[b]thiophen-2-yl)-5-chloropyrimidin-2-amine | 435, 437 | |
| 120 | N-(2-(1H-1,2,3-Triazol-1-yl)ethyl)-4-(7-bromobenzo[b]thiophen-2-yl)-5-methylpyrimidin-2-amine | 415, 417 | |
| 121 | tert-Butyl 2-(4-fluoro-2-(2-(5-fluoro-2-(2-(4-methyl-1H-1,2,3-triazol-1-yl)ethylamino)pyrimidin-4-yl)benzo[b]thiophen-7-yl)phenyl)ethylcarbamate | 592 | |
| 122 | (R)-tert-Butyl 1-(4-fluoro-2-(2-(5-fluoro-2-(2-(4-methyl-1H-1,2,3-triazol-1-yl)ethylamino)pyrimidin-4-yl)benzo[b]thiophen-7-yl)phenyl)ethylcarbamate | 592 | From chiral intermediate |
| 123 | tert-Butyl 1-(4-fluoro-2-(2-(5-fluoro-2-(2-(5-methyl-1H-1,2,3-triazol-1-yl)ethylamino)pyrimidin-4-yl)benzo[b]thiophen-7-yl)phenyl)ethylcarbamate | 592 | |
| 124 | (R)-tert-Butyl 1-(4-fluoro-2-(2-(5-fluoro-2-(2-(5-methyl-1H-1,2,3-triazol-1-yl)ethylamino)pyrimidin-4-yl)benzo[b]thiophen-7-yl)phenyl)ethylcarbamate | 592 | From chiral intermediate |
| 125 | tert-Butyl 1-(4-fluoro-2-(2-(5-fluoro-2-(2-(4-(hydroxymethyl)-1H-1,2,3-triazol-1-yl)ethylamino)pyrimidin-4-yl)benzo[b]thiophen-7-yl)phenyl)ethylcarbamate | 608 | |
| 126 | tert-Butyl 1-(4-fluoro-2-(2-(5-fluoro-2-(2-(5-(hydroxymethyl)-1H-1,2,3-triazol-1-yl)ethylamino)pyrimidin-4-yl)benzo[b]thiophen-7-yl)phenyl)ethylcarbamate | 608 | |

Prepare the following intermediates with procedures similar to those described for N-(2-(1H-1,2,3-Triazol-1-yl)ethyl)-5-fluoro-4-(7-(5-fluoro-1H-indol-7-yl)benzo[b]thiophen-2-yl)pyrimidin-2-amine below:

| Prep | Compound Name | MS (ES) m/z [M + 1]+ |
|---|---|---|
| 127 | [1-(4-Fluoro-2-{2-[5-fluoro-2-(2-[1,2,3]triazol-1-yl-ethylamino)-pyrimidin-4-yl]-benzo[b]thiophen-7-yl}-phenyl)-ethyl]-carbamic acid tert-butyl ester | 578 |
| 128 | tert-Butyl 1-(2-(2-(2-(2-(1H-1,2,3-triazol-1-yl)ethylamino)-5-fluoropyrimidin-4-yl)benzo[b]thiophen-7-yl)-4-fluorophenyl)-2,2,2-trifluoroethyl(methyl)carbamate | 646 |
| 129 | N-(2-(2-(2-(2-(1H-1,2,3-Triazol-1-yl)ethylamino)-5-fluoropyrimidin-4-yl)benzo[b]thiophen-7-yl)-4-fluorophenyl)propan-2-yl)formamide | 520 |
| 130 | tert-Butyl 1-(2-(2-(2-(2-(1H-1,2,3-triazol-1-yl)ethylamino)-5-fluoropyrimidin-4-yl)benzo[b]thiophen-7-yl)-4-fluorophenyl)propylcarbamate | 592 |
| 131 | tert-Butyl 2-(2-(2-(2-(2-(1H-1,2,3-triazol-1-yl)ethylamino)-5-fluoropyrimidin-4-yl)benzo[b]thiophen-7-yl)-4-fluorophenyl)aziridine-1-carboxylate | MS (ES) [M]+ 575 |
| 132 | tert-Butyl 1-(2-(2-(2-(2-(1H-1,2,3-triazol-1-yl)ethylamino)-5-methylpyrimidin-4-yl)benzo[b]thiophen-7-yl)-4-fluorophenyl)ethyl(methyl)carbamate | 588 |
| 133 | tert-Butyl 1-(2-(2-(2-(2-(1H-1,2,3-triazol-1-yl)ethylamino)pyrimidin-4-yl)benzo[b]thiophen-7-yl)-4-fluorophenyl)ethyl(methyl)carbamate | 574 |
| 134 | tert-Butyl 1-(2-(2-(2-(2-(1H-1,2,3-triazol-1-yl)ethylamino)pyrimidin-4-yl)benzo[b]thiophen-7-yl)-4-fluorophenyl)ethyl(methyl)carbamate | 574 |
| 135 | tert-Butyl 1-(2-(2-(2-(2-(1H-1,2,3-triazol-1-yl)ethylamino)-5-fluoropyrimidin-4-yl)benzo[b]thiophen-7-yl)-4-fluorophenyl)cyclobutylcarbamate | 602 (M − 1)− |
| 136 | tert-Butyl 2-(2-(2-(2-(2-(1H-1,2,3-triazol-1-yl)ethylamino)-5-fluoropyrimidin-4-yl)benzo[b]thiophen-7-yl)-4-fluorophenyl)pyrrolidine-1-carboxylate | 604 |
| 137 | 1-(2-(2-(2-(2-(1H-1,2,3-Triazol-1-yl)ethylamino)-5-fluoropyrimidin-4-yl)benzo[b]thiophen-7-yl)-4-fluorophenyl)ethanone | 477 |

PREPARATION 138

[2-(2-{2-[5-Fluoro-2-(2-[1,2,3]triazol-1-yl-ethylamino)-pyrimidin-4-yl]-benzo[b]thiophen-7-yl}-phenyl)-ethyl]-carbamic acid tert-butyl ester Add a solution of 2 M sodium carbonate (1.08 mL, 2.16 mmol) to a suspension of {2-[2-(4,4,5,5-tetramethyl-[1,3,2]dioxaborolan-2-yl)-phenyl]-ethyl}-carbamic acid tert-butyl ester (0.5 g, 1.08 mmol), [4-(7-bromo-benzo[b]thiophen-2-yl)-5-fluoro-pyrimidin-2-yl]-(2-[1,2,3]triazol-1-yl-ethyl)-amine (450 mg, 1.08 mmol), and Pd(dppf)Cl$_2$ (45 mg, 53.99 μmol) in 1,4-dioxane (4.32 mL) and heat at 100° C. for 4 h. Cool to RT and concentrate. Suspend the residue in DCM and filter through a 2-cm pad of silica in a 60-mL sintered glass funnel Elute with 50 mL DCM and 50 mL (1:1 ethyl acetate/hexane). Then elute with 200 mL of ethyl acetate to collect the product. Concentrate and purify on silica eluting with 10% ethanol in 1:1 DCM/hexane to give the title compound. MS (ES) m/z 560 [M+1]+.

Prepare the following intermediates with procedures similar to those described for [2-(2-{2-[5-Fluoro-2-(2-[1,2,3]triazol-1-yl-ethylamino)-pyrimidin-4-yl]-benzo[b]thiophen-7-yl}-phenyl)-ethyl]-carbamic acid tert-butyl ester:

| Prep | Compound Name | MS (ES) m/z [M + 1]+ |
|---|---|---|
| 139 | 2-{2-[5-Fluoro-2-(2-[1,2,3]triazol-1-yl-ethylamino)-pyrimidin-4-yl]-benzo[b]thiophen-7-yl}-benzaldehyde | 445 |

PREPARATION 140

(9H-Fluoren-9-yl)methyl(R)-1-((R)-1-(2-(2-(2-(2-(1H-1,2,3-triazol-1-yl)ethylamino)-5-fluoropyrimidin-4-yl)benzo[b]thiophen-7-yl)-4-fluorophenyl)ethylamino)-1-oxopropan-2-ylcarbamate Add diisopropylethylamine (43 mg, 335 μmol) to a solution of (R)—N-(2-(1H-1,2,3-triazol-1-yl)ethyl)-4-(7-(2-(1-aminoethyl)-5-fluorophenyl)benzo[b]thiophen-2-yl)-5-fluoropyrimidin-2-amine (80 mg, 167 μmol), (9-fluorenylmethoxycarbonyl)-D-alanine-chloride (83 mg, 251 μmol) in 1,4-dioxane (5 mL). Stir the mixture at RT for 3 h. Dilute the mixture with chloroform/IPA (3/1, 100 mL), wash with water/aqueous saturated sodium chloride, dry over sodium sulfate, and concentrate in vacuo. Purify the crude product by FCC (10% methanol in DCM as elute) to give the title compound as a yellow solid (129 mg, 100%). MS (ES) m/z 770 [M+1]+.

EXAMPLE 1

2-(2-(2-(2-(2-(1H-1,2,3-Triazol-1-yl)ethylamino)-5-fluoropyrimidin-4-yl)benzo[b]thiophen-7-yl)phenoxy)ethnol

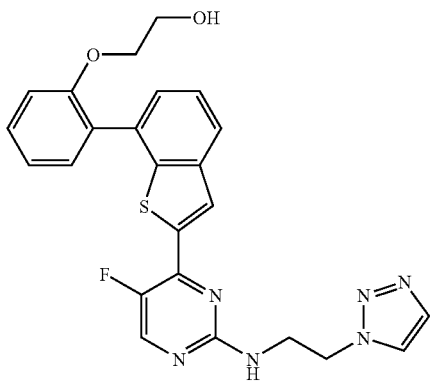

Combine 2-chloro-5-fluoro-4-(7-{2-[2-(tetrahydro-pyran-2-yloxy)-ethoxy]-phenyl}-benzo[b]thiophen-2-yl)-pyrimidine (250 mg, 0.52 mmol) and 2-[1,2,3]triazol-1-yl-ethylamine (140 mg, 1.29 mmol) in tert-butanol (2.6 mL, alternative dioxane, n-butanol, dioxane-NMP, NMP alone as solvent) and NMP (1.3 mL) in a pressure vessel. Heat the mixture in an oil bath at 120-150° C. overnight (or in microwave reactor for a certain period of time). Dilute the mixture with chloroform/IPA (3/1). Wash the solution with aqueous saturated sodium chloride. Dry over sodium sulfate. Concentrate the solution in vacuo. Purify by column chromatography (DCM to 10% methanol in DCM) to give the title compound as a yellow solid (160 mg, 65%). MS (ES) m/z 477 [M+1]$^+$.

Prepare the following examples with procedures similar to those described for 2-(2-{2-[5-Fluoro-2-(2-[1,2,3]triazol-1-yl-ethylamino)-pyrimidin-4-yl]-benzo[b]thiophen-7-yl}-phenoxy)-ethanol:

| Ex | Compound structure | Compound Name | MS (ES) m/z [M + 1]$^+$ | Comments |
|---|---|---|---|---|
| 2 | 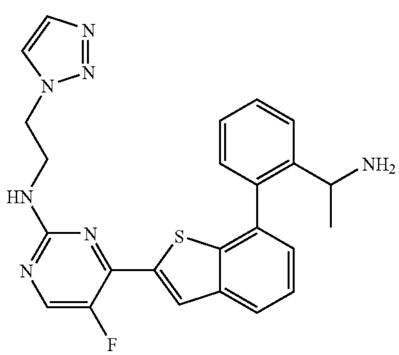 | N-(2-(1H-1,2,3-Triazol-1-yl)ethyl)-4-(7-(2-(1-aminoethyl)phenyl)benzo[b]thiophen-2-yl)-5-fluoropyrimidin-2-amine | 460 | |
| 3 | 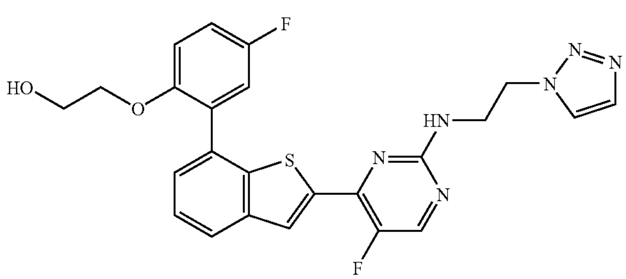 | 2-(2-(2-(2-(2-(1H-1,2,3-Triazol-1-yl)ethylamino)-5-fluoropyrimidin-4-yl)benzo[b]thiophen-7-yl)-4-fluorophenoxy)ethanol | 495 | |
| 4 | 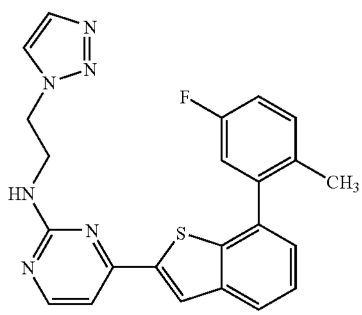 | N-(2-(1H-1,2,3-Triazol-1-yl)ethyl)-4-(7-(5-fluoro-2-methylphenyl)benzo[b]thiophen-2-yl)pyrimidin-2-amine | 431 | |

-continued

| Ex | Compound structure | Compound Name | MS (ES) m/z [M + 1]+ | Comments |
|---|---|---|---|---|
| 5 | 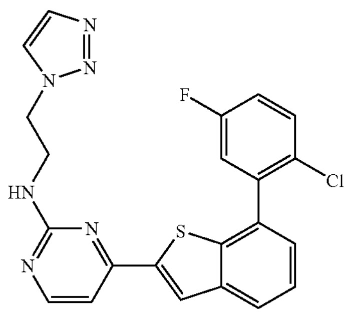 | N-(2-(1H-1,2,3-Triazol-1-yl)ethyl)-4-(7-(2-chloro-5-fluorophenyl)benzo[b]thiophen-2-yl)pyrimidin-2-amine | 451 | |
| 6 | 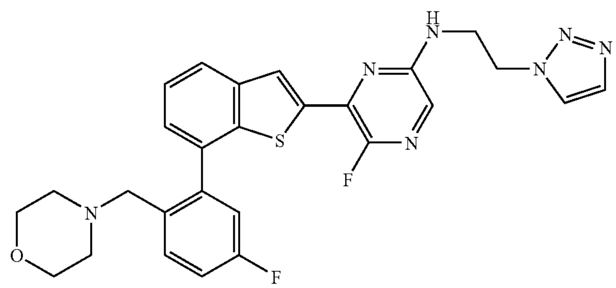 | N-(2-(1H-1,2,3-Triazol-1-yl)ethyl)-5-fluoro-4-(7-(5-fluoro-2-(morpholinomethyl)phenyl)benzo[b]thiophen-2-yl)pyrimidin-2-amine | 534 | |
| 7 | 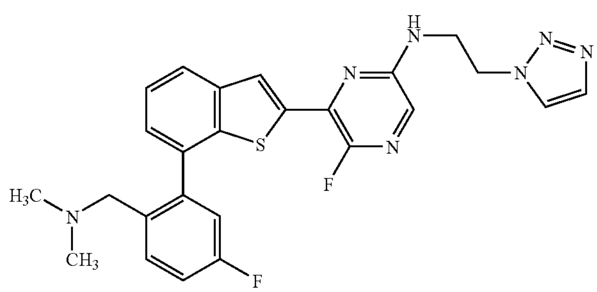 | N-(2-(1H-1,2,4-Triazol-1-yl)ethyl)-4-(7-(2-((dimethylamino)methyl)-5-fluorophenyl)benzo[b]thiophen-2-yl)-5-fluoropyrimidin-2-amine | 492 | |
| 8 | 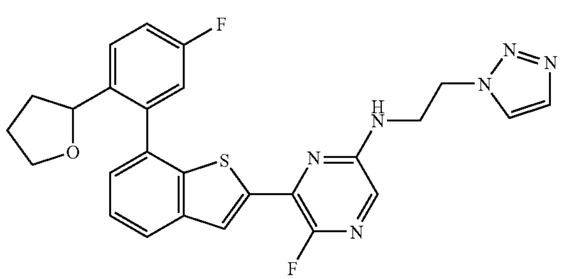 | N-(2-(1H-1,2,3-Triazol-1-yl)ethyl)-5-fluoro-4-(7-(5-fluoro-2-(tetrahydrofuran-2-yl)phenyl)benzo[b]thiophen-2-yl)pyrimidin-2-amine | 505 | |
| 9 | 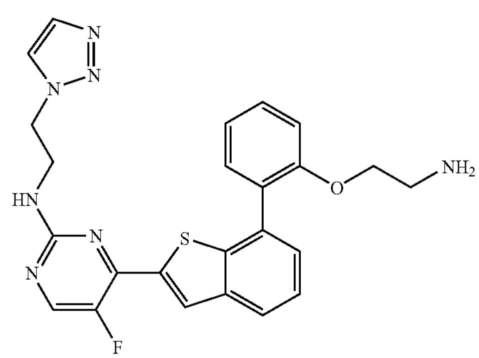 | N-(2-(1H-1,2,3-Triazol-1-yl)ethyl)-4-(7-(2-(2-aminoethoxy)phenyl)benzo[b]thiophen-2-yl)-5-fluoropyrimidin-2-amine | 476 | Use TFA to remove Boc |

-continued

| Ex | Compound structure | Compound Name | MS (ES) m/z [M + 1]⁺ | Comments |
|---|---|---|---|---|
| 10 | 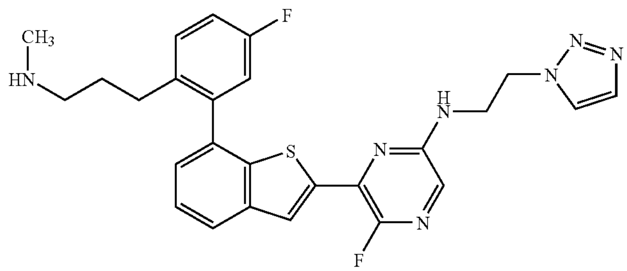 | N-(2-(1H-1,2,3-Triazol-1-yl)ethyl)-5-fluoro-4-(7-(5-fluoro-2-(2-(methyl-amino)ethoxy)phenyl)-benzo[b]thiophen-2-yl)primidin-2-amine | 508 | Use TFA to remove Boc |
| 11 | 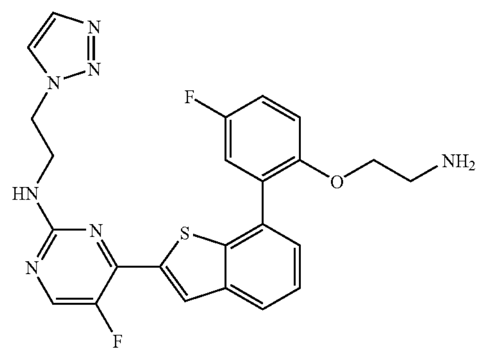 | N-(2-(1H-1,2,3-Triazol-1-yl)ethyl)-4-(7-(2-(2-aminoethoxy)-5-fluoro-phenyl)benzo[b]thiophen-2-yl)-5-fluoropyrimidin-2-amine | 494 | Use TFA to remove Boc |
| 12 | 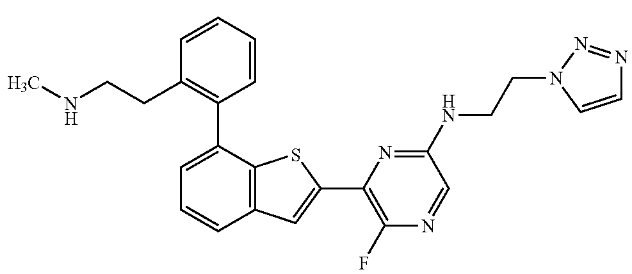 | N-(2-(1H-1,2,3-Triazol-1-yl)ethyl)-5-fluoro-4-(7-(2-(2-(methylamino)ethyl)-phenyl)benzo[b]thiophen-2-yl)pyrimidin-2-amine | 474 | Use TFA to remove Boc |
| 13 | 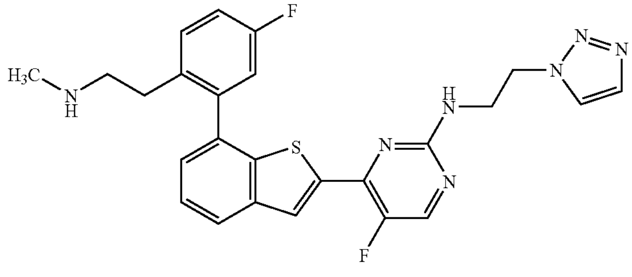 | N-(2-(1H-1,2,3-Triazol-1-yl)ethyl)-5-fluoro-4-(7-(5-fluoro-2-(2-(methyl-amino)ethyl)phenyl)benzo[b]thiophen-2-yl)pyrimidin-2-amine | 492 | Use TFA to remove Boc |

EXAMPLE 14

N-(2-(1H-1,2,3-Triazol-1-yl)ethyl)-5-fluoro-4-(7-(5-fluoro-1H-indol-7-yl)benzo[b]thiophen-2-yl)pyrimidin-2-amine

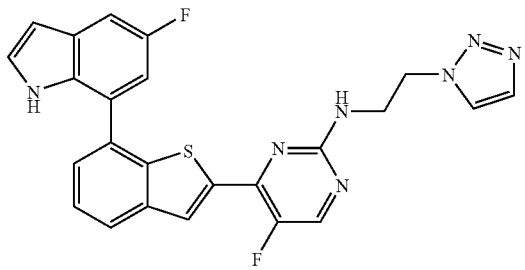

Combine N-(2-(1H-1,2,3-triazol-1-yl)ethyl)-5-fluoro-4-(7-(4,4,5,5-tetramethyl-1,3,2-dioxaborolan-2-yl)benzo[b]thiophen-2-yl)pyrimidin-2-amine (0.12 g, 0.26 mmol), 7-bromo-5-fluoro-1H-indole (64 mg, 0.28 mmol, synthesized based on reference: Manfred S.; Assunta G.; Frédéric L., *Eur. J. Org. Chem.* 2006, 2956-2069), barium hydroxide octahydrate (0.24 g, 0.77 mmol, alternatively sodium carbonate, potassium carbonate, cesium fluoride), Pd(dppf)Cl$_2$ (20 mg, 0.03 mmol) in 2 mL of mixed solvent of DMF (alternatively dioxane, DMSO) and water (4/1, v/v). Purge the mixture with N$_2$ three times. Heat the reaction mixture to 80° C. for 4 h (HPLC monitor) (or microwave reactor). Cool to RT. Dilute with chloroform/IPA (3:1, v/v) 50 mL. Wash with water, aqueous saturated sodium chloride and dry over magnesium sulfate. Remove the organic solvent to give the crude product. Purify the residue by column chromatography (hexane to ethyl acetate, or methylene chloride and methanol) to give the title compound (0.053 g, 43%). MS (ES) m/z 474 [M+1]$^+$.

Prepare the following examples with procedures similar to those described for N-(2-(1H-1,2,3-Triazol-1-yl)ethyl)-5-fluoro-4-(7-(5-fluoro-1H-indol-7-yl)benzo[b]thiophen-2-yl)pyrimidin-2-amine:

| Ex | Compound structure | Compound Name | MS (ES) m/z [M + 1]$^+$ | Comments |
|---|---|---|---|---|
| 15 | 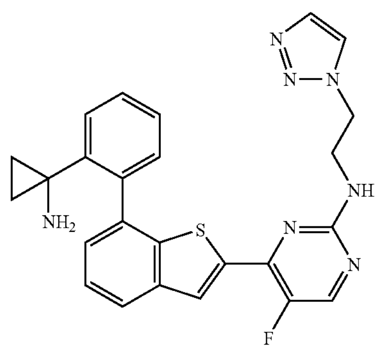 | N-(2-(1H-1,2,3-Triazol-1-yl)ethyl)-4-(7-(2-(1-aminocyclopropyl)-phenyl)benzo[b]thiophen-2-yl)-5-fluoropyrimidin-2-amine | 472 | 1-(2-Bromophenyl)-cyclopropylamine: *J. Org. Chem.* 2003, 68, 7133 |
| 16 | 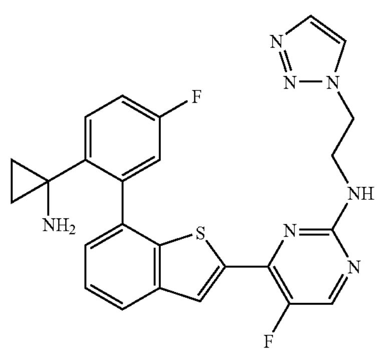 | N-(2-(1H-1,2,3-Triazol-1-yl)ethyl)-4-(7-(2-(1-aminocyclopropyl)-5-fluorophenyl)benzo[b]thiophen-2-yl)-5-fluoropyrimidin-2-amine | 490 | |

-continued

| Ex | Compound structure | Compound Name | MS (ES) m/z [M + 1]+ | Comments |
|---|---|---|---|---|
| 17 | 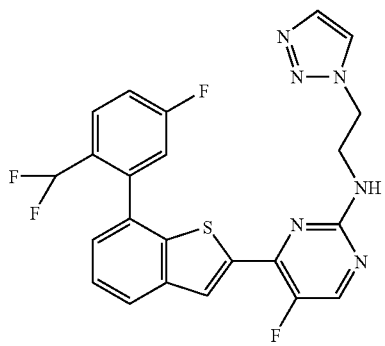 | N-(2-(1H-1,2,3-Triazol-1-yl)ethyl)-4-(7-(2-(difluoro-methyl)-5-fluorophenyl)-benzo[b]thiophen-2-yl)-5-fluoropyrimidin-2-amine | 485 | |
| 18 | 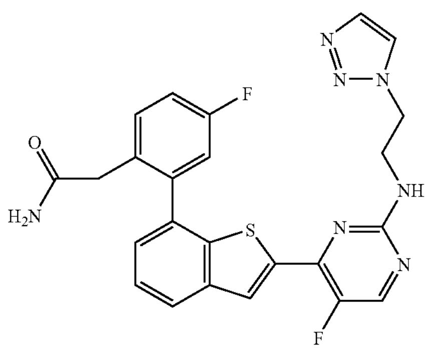 | 2-(2-(2-(2-(2-(1H-1,2,3-Triazol-1-yl)ethylamino)-5-fluoropyrimidin-4-yl)benzo[b]thiophen-7-yl)-4-fluorophenyl)-acetamide | 492 | |
| 19 | 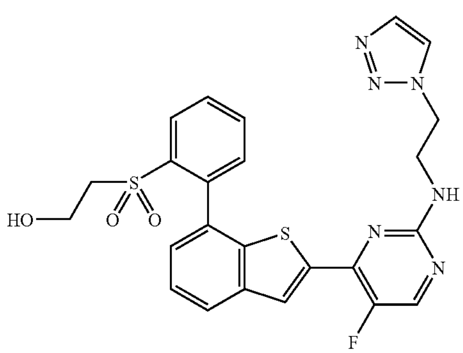 | 2-(2-(2-(2-(2-(1H-1,2,3-Triazol-1-yl)ethylamino)-5-fluoropyrimidin-4-yl)benzo[b]thiophen-7-yl)phenylsulfonyl)ethanol | 525 | |
| 20 | 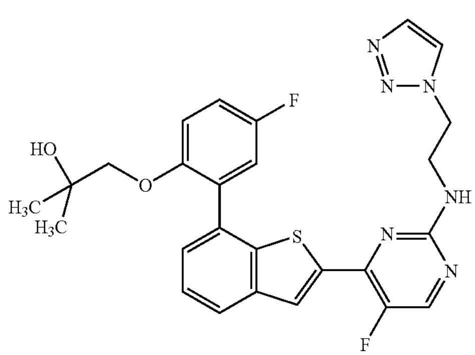 | 1-(2-(2-(2-(2-(1H-1,2,3-Triazol-1-yl)ethylamino)-5-fluoropyrimidin-4-yl)benzo[b]thiophen-7-yl)-4-fluorophenoxy)-2-methylpropan-2-ol | 523 | |

-continued

| Ex | Compound structure | Compound Name | MS (ES) m/z [M + 1]+ | Comments |
|---|---|---|---|---|
| 21 | 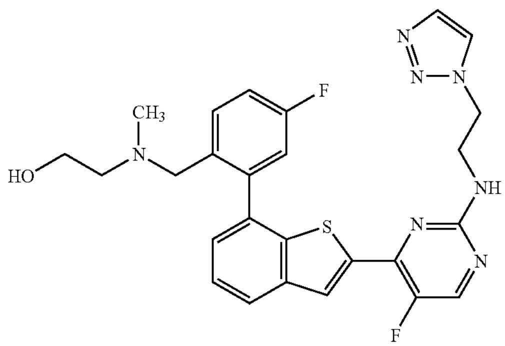 | 2-((2-(2-(2-(2-(1H-1,2,3-Triazol-1-yl)ethylamino)-5-fluoropyrimidin-4-yl)benzo[b]thiophen-7-yl)-4-fluorobenzyl)-(methyl)-amino)ethanol | 522 | |
| 22 | 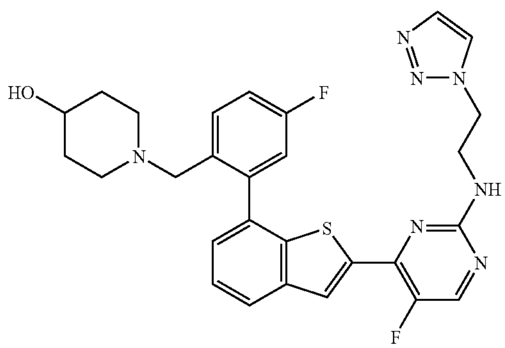 | 1-(2-(2-(2-(2-(1H-1,2,3-Triazol-1-yl)ethylamino)-5-fluoropyrimidin-4-yl)benzo[b]thiophen-7-yl)-4-fluorobenzyl)piperidin-4-ol | 548 | |
| 23 | 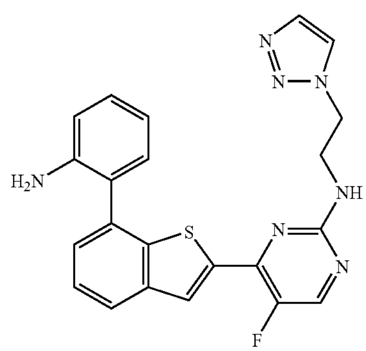 | N-(2-(1H-1,2,3-Triazol-1-yl)ethyl)-4-(7-(2-amino-phenyl)benzo[b]thiophen-2-yl)-5-fluoropyrimidin-2-amine | 432 | Purify by reverse phase |
| 24 | 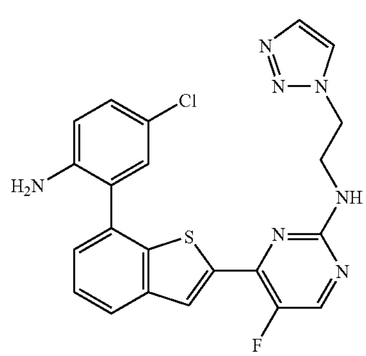 | N-(2-(1H-1,2,3-Triazol-1-yl)ethyl)-4-(7-(2-amino-5-chlorophenyl)benzo[b]thiophen-2-yl)-5-fluoropyrimidin-2-amine | 466 | Purify by reverse phase |

-continued

| Ex | Compound structure | Compound Name | MS (ES) m/z [M + 1]+ | Comments |
|---|---|---|---|---|
| 25 | 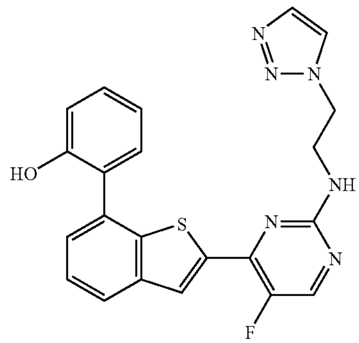 | 2-(2-(2-(2-(1H-1,2,3-Triazol-1-yl)ethylamino)-5-fluoropyrimidin-4-yl)benzo[b]thiophen-7-yl)phenol | 433 | Purify by reverse phase |
| 26 | 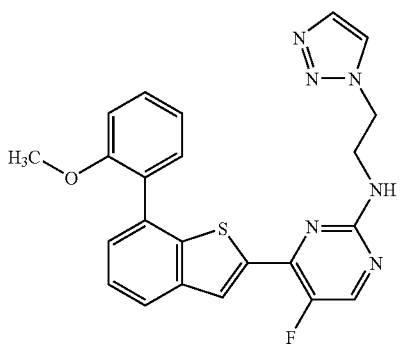 | N-(2-(1H-1,2,3-Triazol-1-yl)ethyl)-5-fluoro-4-(7-(2-methoxyphenyl)-benzo[b]thiophen-2-yl)pyrimidin-2-amine | 447 | Purify by reverse phase |
| 27 | 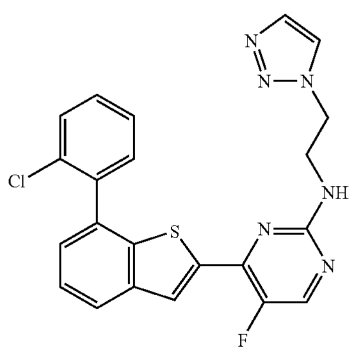 | N-(2-(1H-1,2,3-Triazol-1-yl)ethyl)-4-(7-(2-chloro-phenyl)benzo[b]thiophen-2-yl)-5-fluoropyrimidin-2-amine | 451 | Purify by reverse phase |
| 28 | 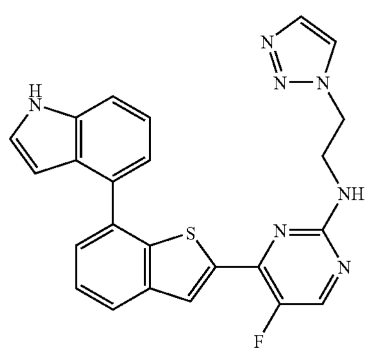 | N-(2-(1H-1,2,3-Triazol-1-yl)ethyl)-4-(7-(1H-indol-4-yl)benzo[b]thiophen-2-yl)-5-fluoropyrimidin-2-amine | 456 | Purify by reverse phase |

-continued

| Ex | Compound structure | Compound Name | MS (ES) m/z [M + 1]+ | Comments |
|---|---|---|---|---|
| 29 | 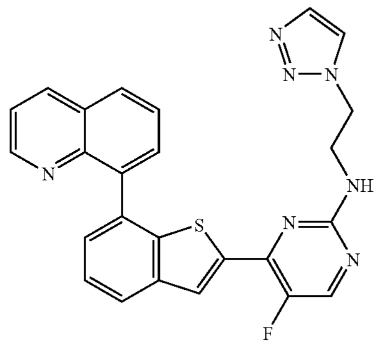 | N-(2-(1H-1,2,3-Triazol-1-yl)ethyl)-5-fluoro-4-(7-(quinolin-8-yl)benzo[b]thiophen-2-yl)pyrimidin-2-amine | 468 | Purify by reverse phase |
| 30 | 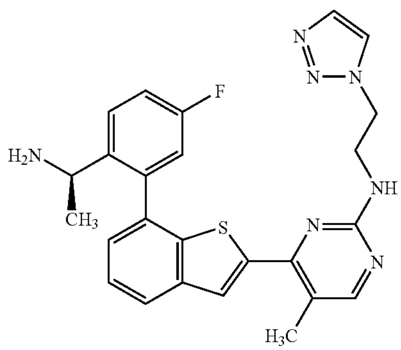 | (R)-N-(2-(1H-1,2,3-Triazol-1-yl)ethyl)-4-(7-(2 (1-aminoethyl)-5-fluoro-phenyl)benzo[b]thiophen-2-yl)-5-methyl-pyrimidin-2-amine | 474 | From chiral intermediate, Use TFA to remove Boc |
| 31 | 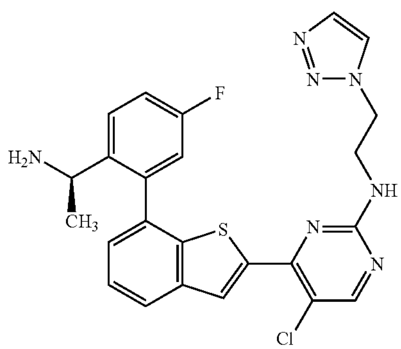 | (R)-N-(2-(1H-1,2,3-Triazol-1-yl)ethyl)-4-(7-(2 (1-aminoethyl)-5-fluoro-phenyl)benzo[b]thiophen-2-yl)-5-chloro-pyrimidin-2 amine | 494 | From chiral intermediate, Use TFA to remove Boc |
| 32 | 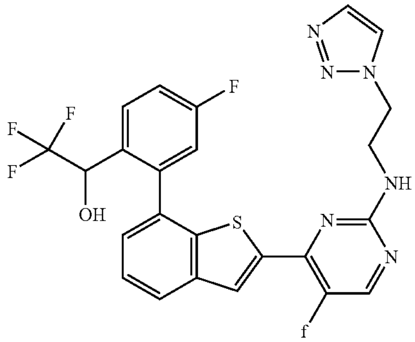 | 1-(2-(2-(2-(2-(1H-1,2,3-Triazol-1-yl)ethylamino)-5-fluoropyrimidin-4-yl)benzo[b]thiophen-7-yl)-4-fluorophenyl)-2,2,2-trifluoroethanol | 533 | |

-continued

| Ex | Compound structure | Compound Name | MS (ES) m/z [M + 1]+ | Comments |
|---|---|---|---|---|
| 33 | 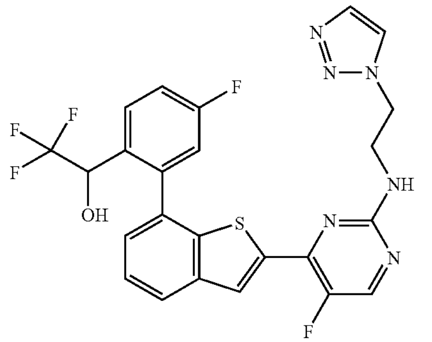 | 1-(2-(2-(2-(2-(1H-1,2,3-Triazol-1-yl)ethylamino)-5-fluoro-pyrimidin-4-yl)benzo[b]thiophen-7-yl) 4-fluorophenyl)-2,2,2-trifluoroethanone | 531 | |
| 34 | 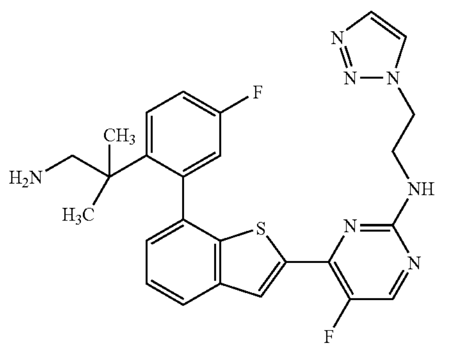 | N-(2-(1H-1,2,3-Triazol-1-yl)ethyl)-4-(7-(2-(1-amino 2-methylpropan-2-yl)-5-fluorophenyl)benzo[b] thiophen-2-yl)-5-fluoropyrimidin-2-amine | 506 | |
| 35 | 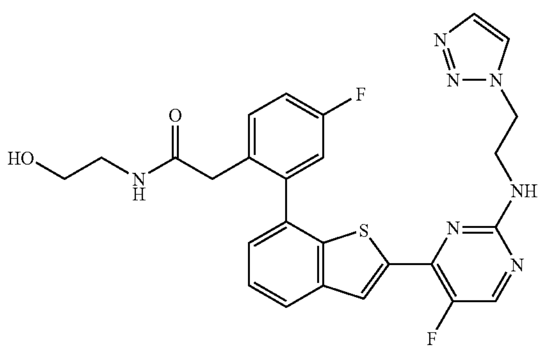 | 2-(2-(2-(2-(2-(1H-1,2,3-Triazol-1-yl)ethylamino)-5-fluoropyrimidin-4-yl)benzo[b]thiophen-7-yl)-4-fluorophenyl)-N-(2-hydroxyethyl)-acetamide | 536 | |
| 36 | 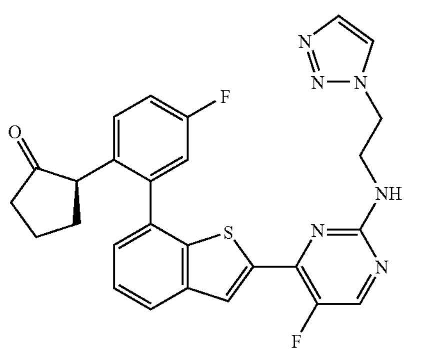 | (R)-2-(2-(2-(2-(2-(1H-1,2,3-Triazol-1-yl)ethylamino)-5-fluoropyrimidin-4-yl)benzo[b]thiophen-7-yl)-4-fluorophenyl)-cyclopentanone | 517 | |

-continued

| Ex | Compound structure | Compound Name | MS (ES) m/z [M + 1]⁺ | Comments |
|---|---|---|---|---|
| 37 | 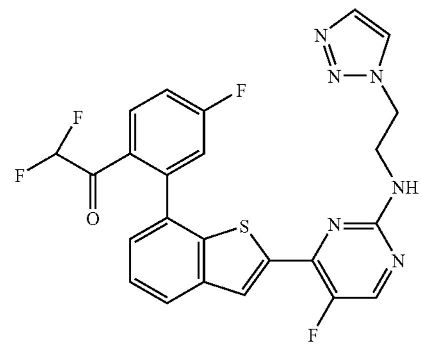 | 1-(2-(2-(2-(2-(1H-1,2,3-Triazol-1-yl)ethylamino)-5-fluoropyrimidin-4-yl)benzo[b]thiophen-7-yl)-4-fluorophenyl)-2,2-difluoro-ethanone | 513 | |
| 38 | 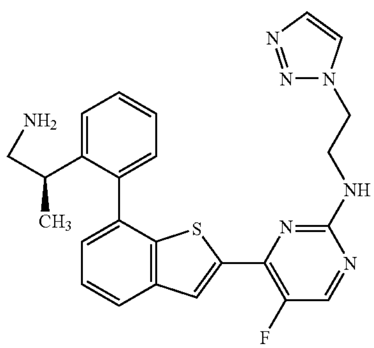 | (R)-N-(2-(1H-1,2,3-Triazol-1-yl)ethyl)-4-(7-(2-(1-aminopropan-2-yl)-phenyl)benzo[b]thiophen-2-yl)-5-fluoropyrimidin-2-amine | 474 | |
| 39 | 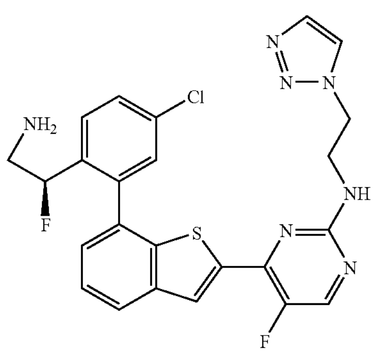 | (R)-N-(2-(1H-1,2,3-Triazol-1-yl)ethyl)-4-(7-(2-(2-amino-1-fluoroethyl)-5-chlorophenyl)benzo[b]thiophen-2-yl)-5-fluoropyrimidin-2-amine | 512 | |
| 40 | 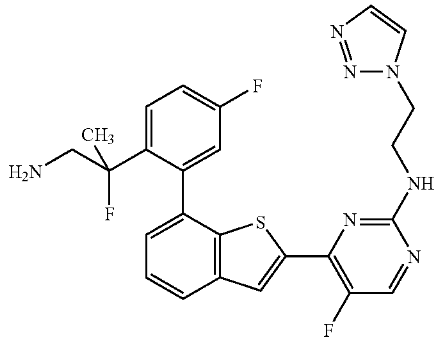 | N-(2-(1H-1,2,3-Triazol-1-yl)ethyl)-4-(7-(2-(1-amino-2-fluoropropan-2-yl)-5-fluorophenyl)benzo[b]thiophen-2-yl)-5-fluoro-pyrimidin-2-amine, hydrochloride | 510 | |

-continued

| Ex | Compound structure | Compound Name | MS (ES) m/z [M + 1]⁺ | Comments |
|---|---|---|---|---|
| 41 | 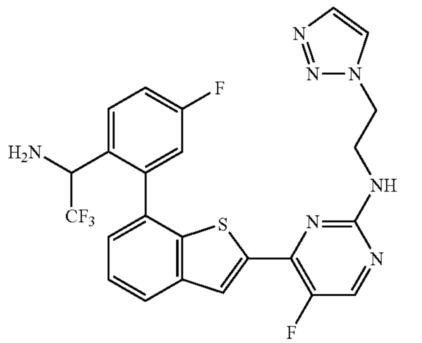 | N-(2-(1H-1,2,3-Triazol-1-yl)ethyl)-4-(7-(2-(1-amino 2,2,2-trifluoroethyl)-5-fluorophenyl)benzo[b]thiophen-2-yl)-5-fluoro-pyrimidin-2-amine | 532 | |
| 42 | 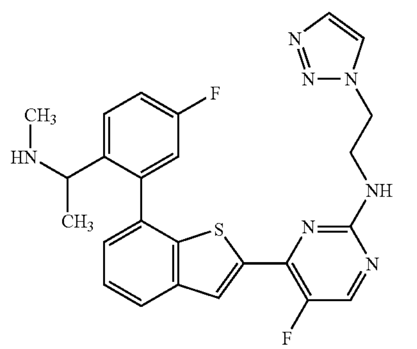 | N-(2-(1H-1,2,3-Triazol-1-yl)ethyl)-5-fluoro-4-(7-(5-fluoro-2-(1-(methylamino)-ethyl)phenyl)benzo[b]thiophen-2-yl) pyrimidin-2-amine | 492 | |
| 43 | 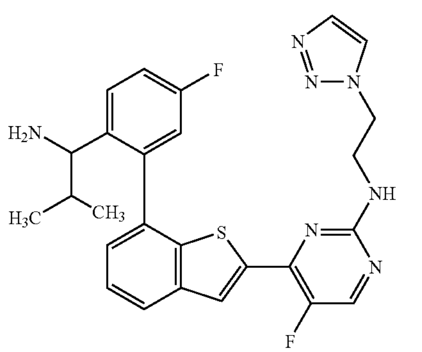 | N-(2-(1H-1,2,3-Triazol-1-yl)ethyl)-4-(7-(2-(1-amino-2-methylpropyl)-5-fluoro-phenyl)benzo[b]thiophen-2-yl)-5-fluoropyrimidin-2-amine | 506 | |
| 44 | 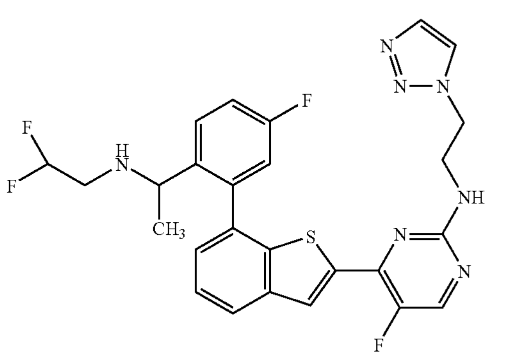 | N-(2-(1H-1,2,3-Triazol-1-yl)ethyl)-4-(7-(2-(1-(2,2-difluoroethyl-amino)ethyl)-5-fluorophenyl)benzo[b]thiophen-2-yl)-5-fluoro-pyrimidin-2-amine | 542 | Purify by reverse phase |

-continued

| Ex | Compound structure | Compound Name | MS (ES) m/z [M + 1]+ | Comments |
|---|---|---|---|---|
| 45 | 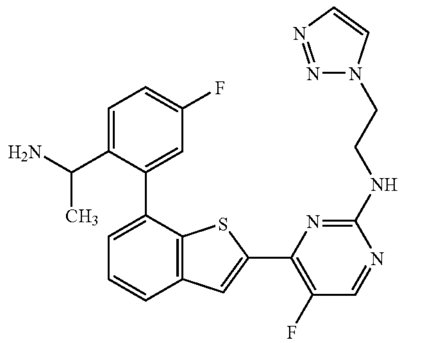 | N-(2-(1H-1,2,3-Triazol-1-yl)ethyl)-4-(7-(2-(1-aminoethyl)-5-chloro-phenyl)benzo[b]thiophen-2-yl)-5-fluoropyrimidin-2-amine | 494 | |

Prepare the following example with procedures similar to those described for [2-(2-{2-[5-Fluoro-2-(2-[1,2,3]triazol-1-yl-ethylamino)-pyrimidin-4-yl]-benzo[b]thiophen-7-yl}-phenyl)-ethyl]-carbamic acid tert-butyl ester above:

| Ex | Compound structure | Compound Name | MS (ES) m/z [M + 1]+ |
|---|---|---|---|
| 46 | 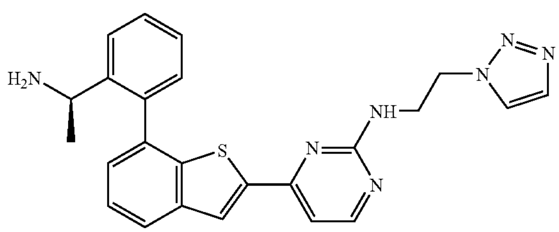 | (R)-N-(2-(1H-1,2,3-Triazol-1-yl)ethyl)-4-(7-(2-(1-aminoethyl)phenyl)benzo[b]thiophen-2-yl)pyrimidin-2-amine | 442 |
| 47 | 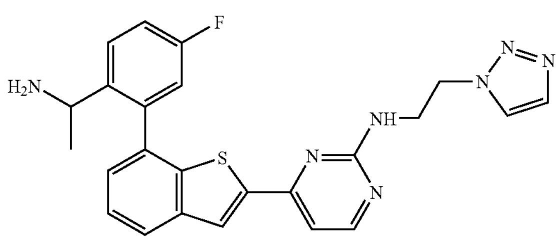 | N-(2-(1H-1,2,3-Triazol-1-yl)ethyl)-4-(7-(2-(1-amino-ethyl)-5-fluorophenyl)-benzo[b]thiophen-2-yl)pyrimidin-2-amine | 460 |
| 48 | 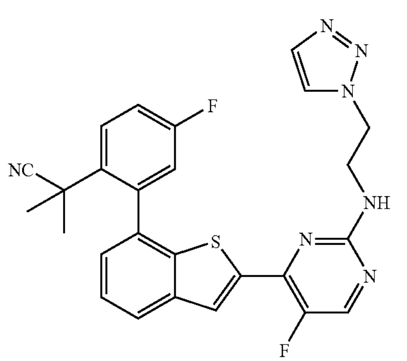 | 2-(2-(2-(2-(2-(1H-1,2,3-Triazol-1-yl)ethylamino)-5-fluoropyrimidin-4-yl)benzo[b]thiophen-7-yl)-4-fluorophenyl)-2-methyl-propanenitrile | 502 |

EXAMPLE 49

N-(2-(1H-1,2,3-Triazol-1-yl)ethyl)-4-(7-(2-(aminomethyl)phenyl)benzo[b]thiophen-2-yl)-5-fluoropyrimidin-2-amine

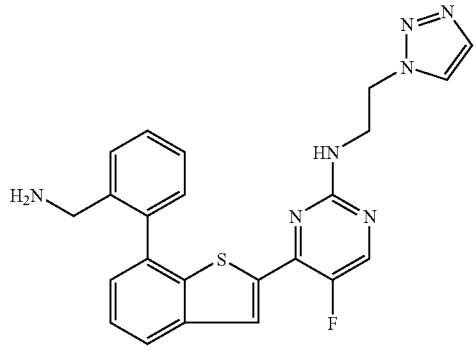

Combine (2-{2-[5-fluoro-2-(2-[1,2,3]triazol-1-yl-ethylamino)-pyrimidin-4-yl]-benzo[b]thiophen-7-yl}-benzyl)-carbamic acid tert-butyl ester (100 mg, 0.18 mmol) and dry TFA acid (2.0 mL) in dry DCM (2.2 mL). Stir the solution at RT for 1 h. Remove the solvent. Add DCM, wash with saturated sodium bicarbonate solution, water, and aqueous saturated sodium chloride. Separate the organic layer and dry over magnesium sulfate. Filter and concentrate in vacuo. Purify the residue by column chromatography [0.1% to 2% 2 M ammonia in methanol/DCM] to give the title compound (78 mg, 96%). MS (ES) m/z 446 [M+1]$^+$.

Prepare the following examples with procedures similar to those described for N-(2-(1H-1,2,3-Triazol-1-yl)ethyl)-4-(7-(2-(aminomethyl)phenyl)benzo[b]thiophen-2-yl)-5-fluoropyrimidin-2-amine:

| Ex | Compound structure | Compound Name | MS (ES) m/z [M + 1]$^+$ | Comments |
|---|---|---|---|---|
| 50 | 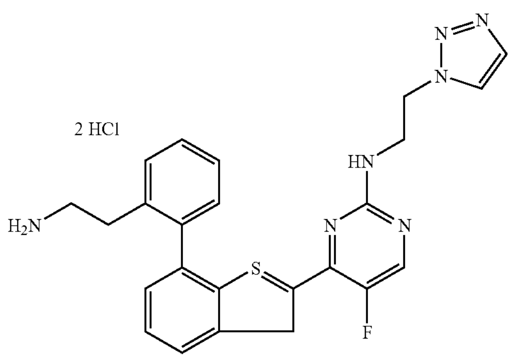 | N-(2-(1H-1,2,3-Triazol-1-yl)ethyl)-4-(7-(2-(2-aminoethyl)phenyl)benzo[b]thiophen-2-yl)-5-fluoropyrimidin-2-amine, dihydrochloride | 460 | Use HCl as acid |
| 51 | 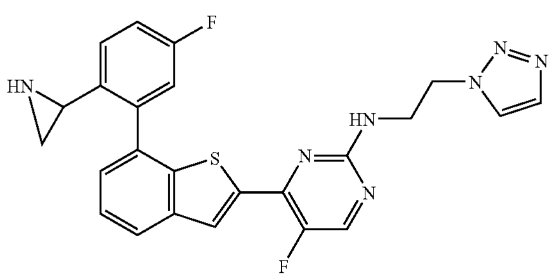 | N-(2-(1H-1,2,3-Triazol-1-yl)ethyl)-4-(7-(2-(aziridin-2-yl)-5-fluorophenyl)-benzo[b]thiophen-2-yl)-5-fluoropyrimidin-2-amine | 476 | |
| 52 | 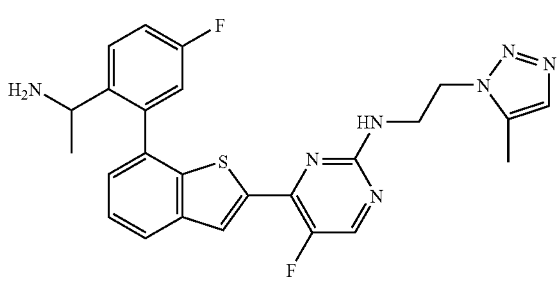 | N-(2-(5-Methyl-1H-1,2,3-triazol-1-yl)ethyl)-4-(7-(2-(1-aminoethyl)-5-fluorophenyl)-benzo[b]thiophen-2-yl)-5-fluoropyrimidin-2-amine | 492 | |

-continued

| Ex | Compound structure | Compound Name | MS (ES) m/z [M + 1]+ | Comments |
|---|---|---|---|---|
| 53 | 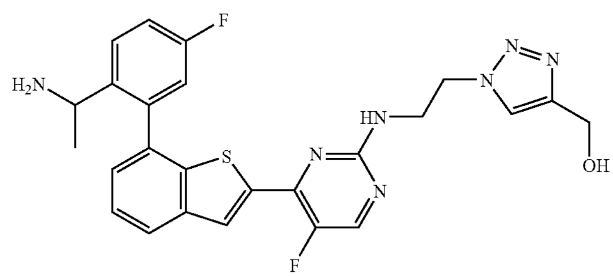 | (1-(2-(4-(7-(2-(1-Aminoethyl)-5-fluoro-phenyl)benzo[b]thiophen-2-yl)-5-fluoro-pyrimidin-2-ylamino)ethyl)-1H-1,2,3-triazol-4-yl)methanol | 508 | |
| 54 | 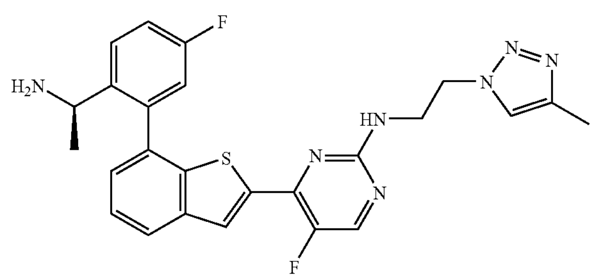 | (R)-N-(2-(4-methyl-1H-1,2,3-Triazol-1-yl)ethyl)-4-(7-(2-(1-aminoethyl)-5-fluoro-phenyl)-benzo[b]thiophen-2-yl)-5-fluoro-pyrimidin-2-amine | 492 | From chiral intermediate |
| 55 | 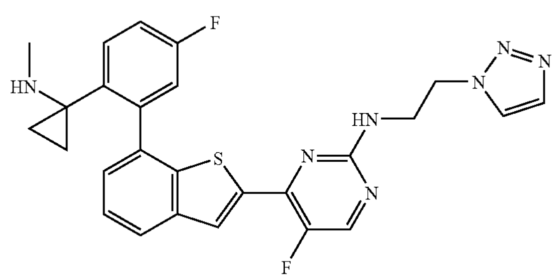 | N-(2-(1H-1,2,3-Triazol-1-yl)ethyl)-5-fluoro-4-(7-(5-fluoro-2-(1-(methyl-amino)cyclopropyl)phenyl)benzo[b]thiophen-2-yl)pyrimidin-2-amine | 504 | |
| 56 | 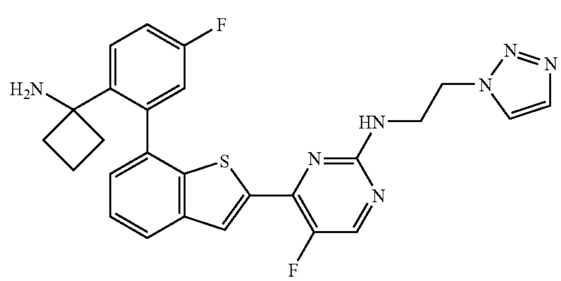 | N-(2-(1H-1,2,3-Triazol-1-yl)ethyl)-4-(7-(2-(1-amino-cyclobutyl)-5-fluoro-phenyl)benzyl[b]thiophen-2-yl)-5-fluoropyrimidin-2-amine | 504 | |
| 57 | 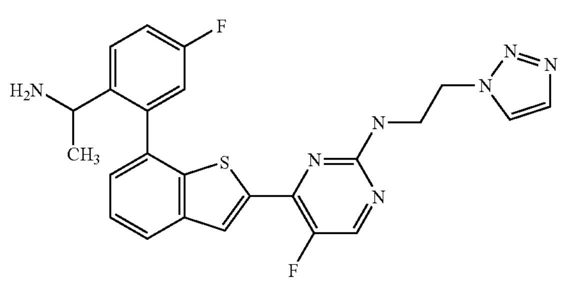 | N-(2-(1H-1,2,3-Triazol-1-yl)ethyl)-4-(7-(2-(1-amino-ethyl)-5-fluorophenyl)-benzo[b]thiophen-2-yl)-5-fluoropyrimidin-2-amine | 478 | |

| Ex | Compound structure | Compound Name | MS (ES) m/z [M + 1]+ | Comments |
|---|---|---|---|---|
| 58 | 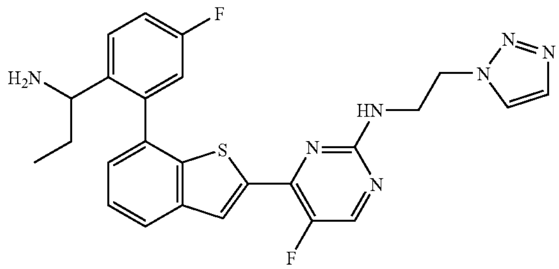 | N-(2-(1H-1,2,3-Triazol-1-yl)ethyl)-4-(7-(2-(1-aminopropyl)-5-fluorophenyl)-benzo[b]thiophen-2-yl)-5-fluoropyrimidin-2-amine | 492 | |
| 59 | 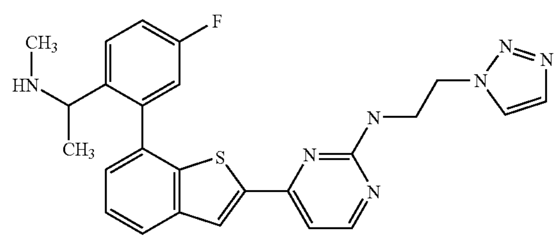 | N-(2-(1H-1,2,3-Triazol-1-yl)ethyl)-4-(7-(5-fluoro-2-(1-(methylamino)ethyl)-phenyl)benzo[b]thiophen-2-yl)pyrimidin-2-amine | 474 | |
| 60 | 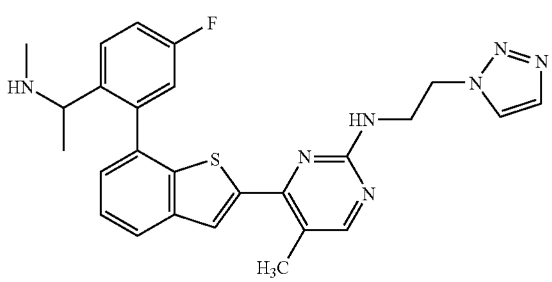 | N-(2-(1H-1,2,3-Triazol-1-yl)ethyl)-4-(7-(5-fluoro-2-(1-(methylamino)ethyl)-phenyl)benzo[b]thiophen-2-yl)-5-methylpyrimidin-2-amine | 488 | |
| 61 | 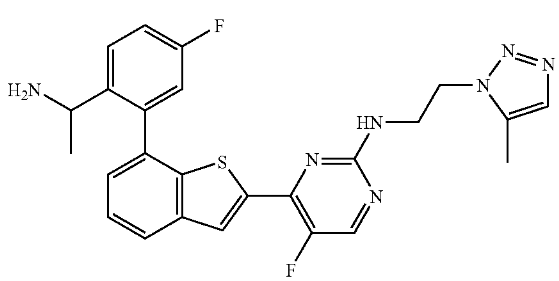 | 4-(7-(2-(1-Aminoethyl)-5-fluorophenyl)benzo[b]thiophen-2-yl)-5-fluoro-N-(2-(5-methyl-1H-1,2,3-triazol-1-yl)ethyl)pyrimidin-2-amine | 492 | |

| Ex | Compound structure | Compound Name | MS (ES) m/z [M + 1]+ | Comments |
|---|---|---|---|---|
| 62 | 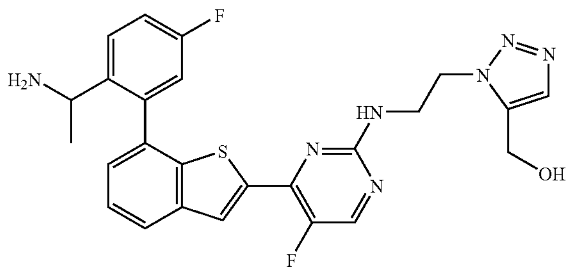 | (1-(2-(4-(7-(2-(1-Amino-ethyl)-5-fluorophenyl)-benzo[b]thiophen-2-yl)-5-fluoropyrimidin-2-yl-amino)ethyl)-1H-1,2,3-triazol-5-yl)methanol | 508 | |
| 63 | 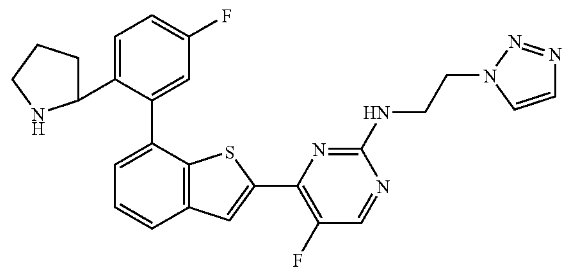 | N-(2-(1H-1,2,3-Triazol-1-yl)ethyl)-5-fluoro-4-(7-(5-fluoro-2-(pyrrolidin-2-yl)-phenyl)benzo[b]thiophen-2-yl)pyrimidin-2-amine | 504 | |
| 64 | 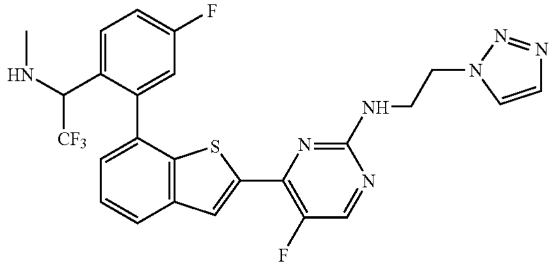 | N-(2-(1H-1,2,3-Triazol-1-yl)ethyl)-5-fluoro-4-(7-(5-fluoro-2-(2,2,2-trifluoro-1-(methylamino)ethyl)-phenyl)benzo[b]thiophen-2-yl)pyrimidin-2-amine | 546 | |

EXAMPLE 65

N-(2-(1H-1,2,3-Triazol-1-yl)ethyl)-5-fluoro-4-(7-(2-((methylamino)methyl)phenyl)benzo[b]thiophen-2-yl)pyrimidin-2-amine

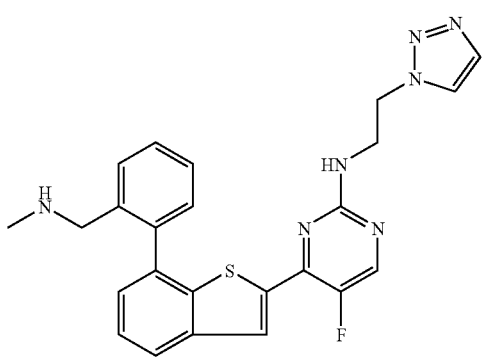

Combine 2-{2-[5-fluoro-2-(2-[1,2,3]triazol-1-yl-ethylamino)-pyrimidin-4-yl]-benzo[b]thiophen-7-yl}-benzaldehyde (800 mg, 1.8 mmol), cyanoborohydride (silica supported, 1 mmol/g, 2.7 g, 2.7 mmol), trimethylacetic acid (0.55 g, 4.7 mmol), and mono-methylamine (0.42 g, 5.4 mmol) in 12 mL of dioxane. Heat the reaction mixture at 100° C. for 20 min in microwave reactor. Cool it to RT. Dilute with chloroform/IPA (3:1, v/v), 50 mL. Wash with water, aqueous saturated sodium chloride, and dry over magnesium sulfate. Remove the organic solvent. Purify the residue by column chromatography [chloroform/methanol/ammonium hydroxide (35% in water), 7/3/0.05] to give the title compound (425 mg, 38%). MS (ES) m/z 460 [M+1]+.

Prepare the following examples with procedures similar to those described for N-(2-(1H-1,2,3-Triazol-1-yl)ethyl)-5-fluoro-4-(7-(2-((methylamino)methyl)phenyl)benzo[b]thiophen-2-yl)pyrimidin-2-amine from the corresponding benzaldehyde or ketone:

| Ex | Compound structure | Compound Name | MS (ES) m/z [M + 1]+ | Comments |
|---|---|---|---|---|
| 66 | 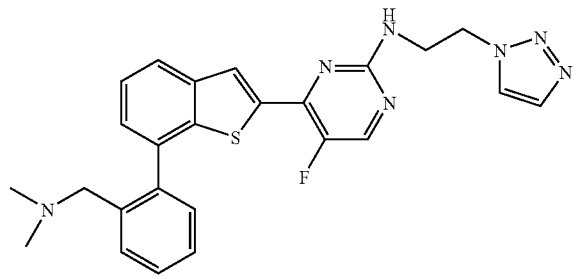 | N-(2-(1H-1,2,3-Triazol-1-yl)ethyl)-4-(7-(2-((dimethylamino)methyl)-phenyl)-benzo[b]thiophen-2-yl)-5-fluoropyrimidin-2-amine | 474 | Use Si-CNH |
| 67 | 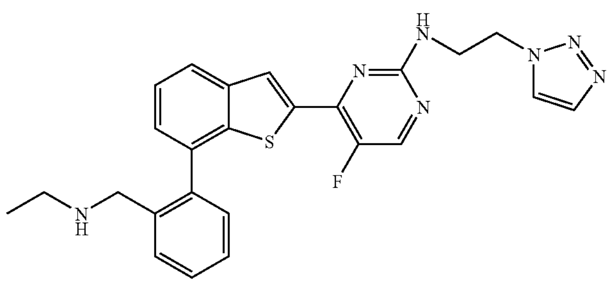 | N-(2-(1H-1,2,3-Triazol-1-yl)ethyl)-4-(7-(2-((ethylamino)methyl)phenyl)-benzo[b]thiophen-2-yl)-5-fluoropyrimidin-2-amine | 474 | Use Si-CNH |
| 68 | 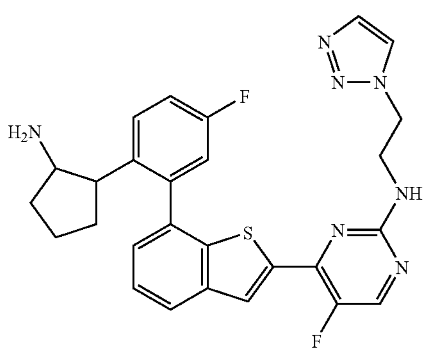 | N-(2-(1H-1,2,3-Triazol-1-yl)ethyl)-4-(7-(2-(2-amino-cyclopentyl)-5-fluoro-phenyl)benzo[b]thiophen-2-yl)-5-fluoropyrimidin-2-amine | 518 | |
| 69 | 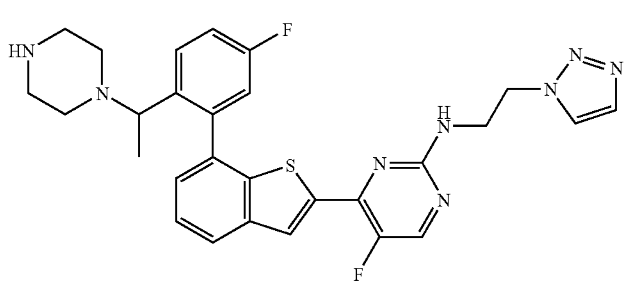 | N-(2-(1H-1,2,3-Triazol-1-yl)ethyl)-5-fluoro-3-(7-(5-fluoro-2-(1-(piperazin-1-yl)ethyl)phenyl)benzo[b]thiophen-2-yl)pyrimidin-2-amine | 547 | |

| Ex | Compound structure | Compound Name | MS (ES) m/z [M + 1]+ | Comments |
|---|---|---|---|---|
| 70 | 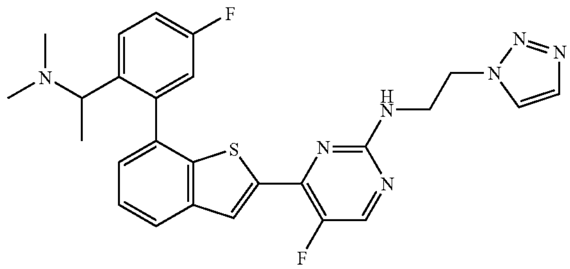 | N-(2-(1H-1,2,3-Triazol-1-yl)ethyl)-4-(7-(2-(1-(dimethylamino)ethyl)-5-fluorophenyl)benzo[b]thiophen-2-yl)-5-fluoro-pyrimidin-2-amine | 506 | |
| 71 | 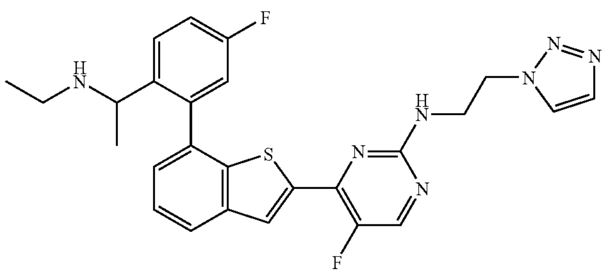 | N-(2-(1H-1,2,3-Triazol-1-yl)ethyl)-4-(7-(2-(1-(ethylamino)ethyl)-5-fluorophenyl)benzo[b]thiophen-2-yl)-5-fluoropyrimidin-2-amine | 506 | |

EXAMPLE 72

2-((1-(2-(2-(2-(2-(1H-1,2,3-Triazol-1-yl)ethylamino)-5-fluoropyrimidin-4-yl)benzo[b]thiophen-7-yl)-4-fluorophenyl)ethyl)(methyl)amino)ethanol

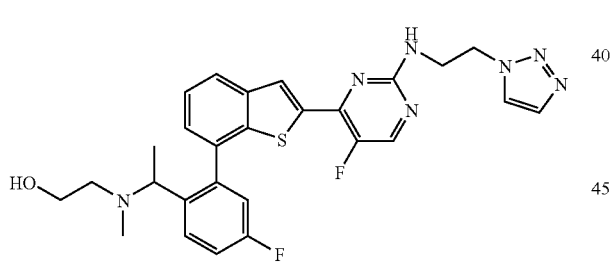

Combine 1-(2-(2-(2-(2-(1H-1,2,3-triazol-1-yl)ethylamino)-5-fluoropyrimidin-4-yl)benzo[b]thiophen-7-yl)-4-fluorophenyl)ethanone (0.1 g, 0.21 mmol), 10% trimethylacetic acid in dioxane (2 mL), 2-(methylamino)ethanol (18.2 mg, 0.252 mmol) and silica-supported cyanoborohydride (0.276 g, 0.262 mmol). Heat the reaction mixture at 160° C. for 2 h in a microwave reactor. Add 2-(methylamino)ethanol (0.157 g, 2.1 mmol) and silica-supported cyanoborohydride (0.138 g, 0.131 mmol). Heat the reaction mixture at 160° C. for 4 h in a microwave reactor. Pour the crude reaction mixture onto a strong cation exchange (SCX) (10 g) column. Elute with 2 N methanolic ammonia (40 mL) and concentrate. Purify the residue by normal phase chromatography (0-100% B at 25 mL/minute for 25 minutes on a 12 g silica column, Solvent A: DCM, Solvent B: 10% 2 N methanolic ammonia in DCM) to give the title compound (41 mg, 36%). MS (ES) m/z 536 [M+1]+.

EXAMPLE 73

(R)—N-(2-(1H-1,2,3-Triazol-1-yl)ethyl)-4-(7-(2-(1-aminoethyl)-5-fluorophenyl)benzo[b]thiophen-2-yl)-5-fluoropyrimidin-2-amine

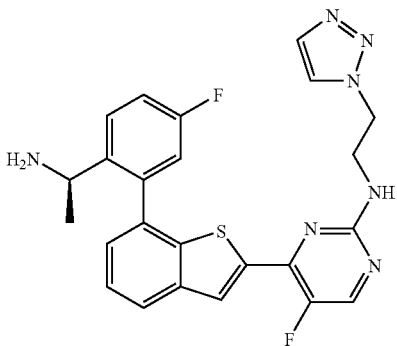

Separate racemic (4-{7-[2-(1-amino-ethyl)-5-fluoro-phenyl]-benzo[b]thiophen-2-yl}-5-fluoro-pyrimidin-2-yl)-(2-[1,2,3]triazol-1-yl-ethyl)-amine (180 mg) by chiral chromatography (Chiralcel® OD-H Column: mobile phase, 40% methanol, 0.2% isopropyl amine in $CO_2$; flow rate, 5 mL/min; detection, 225 nm) to give the title compound (61 mg, 33%). MS (ES) m/z 478 [M+1]+. Alternatively use chiral HPLC Chiralpak® AS-H column (100% MeOH/0.02% dimethylethylamine (DMEA)\$CO_2$, 5 mL/min, 225 nm). Determine the chirality by Vibration Circular Dichroic (VCD) spectroscopy.

Separate the following examples from their racemates by utilizing chiral chromatographic methods similar to the ones listed above:

| Ex | Compound structure | Compound Name | MS (ES) m/z [M + 1]+ | Comments |
|---|---|---|---|---|
| 74 | 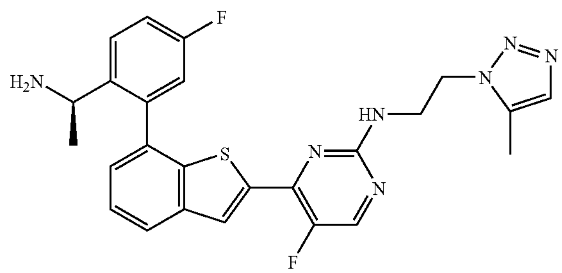 | (R)-N-(2-(5-Methyl-1H-1,2,3-triazol-1-yl)ethyl)-4-(7-(5-fluoro-2-(1-amino-ethyl)-phenyl)-benzo[b]thiophen-2-yl)-5-fluoro-pyrimidin-2-amine | 492 | Chiralpak ® AS-H |
| 75 | 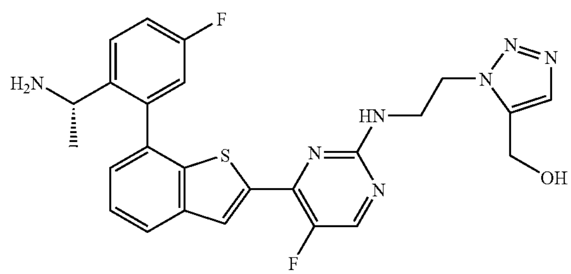 | (S)-1-(2-(4-(7-(2-(1-Aminoethyl)-5-fluorophenyl)benzo[b]thiophen-2-yl)-5-fluoropyrimidin-2-ylamino)ethyl)-1H-1,2,3-triazol-5-yl)methanol | 508 | Chiralcel ® OD-H |
| 76 | 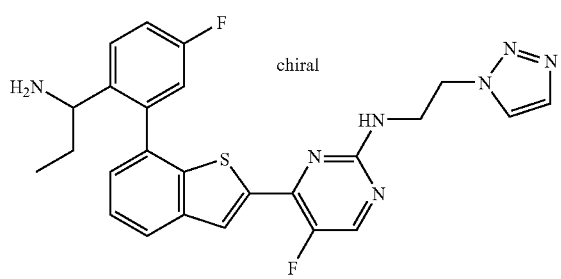 | N-(2-(1H-1,2,3-Triazol-1-yl)ethyl)-4-(7-(2-(1-amino-propyl)-5-fluorophenyl)-benzo[b]thiophen-2-yl)-5-fluoropyrimidin-2-amine | 492 | Chiralpak ® AS-H, first fraction |
| 77 | 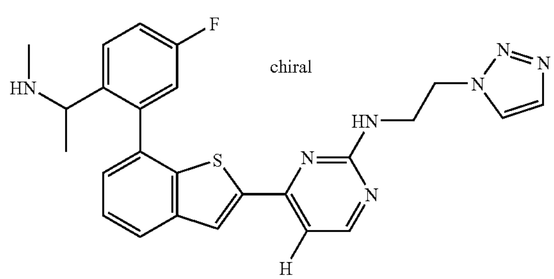 | N-(2-(1H-1,2,3-Triazol-1-yl)ethyl)-4-(7-(5-fluoro-2-(1-(methylamino)ethyl)-phenyl)benzo[b]thiophen-2-yl)pyrimidin-2-amine | 474 | Chiral OJ-H, first fraction |
| 78 | 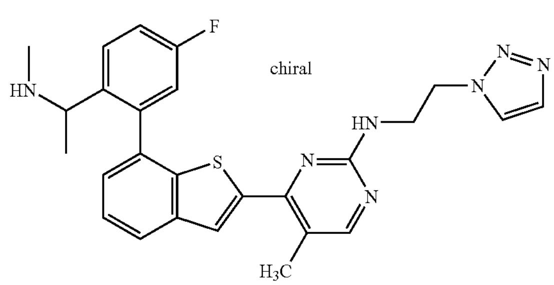 | N-(2-(1H-1,2,3-Triazol-1-yl)ethyl)-4-(7-(5-fluoro-2-(1-(methylamino)ethyl)-phenyl)benzo[b]thiophen-2-yl)-5-methylpyrimidin-2-amine | 488 | Chiral OJ-H, first fraction |

-continued

| Ex | Compound structure | Compound Name | MS (ES) m/z [M + 1]+ | Comments |
|---|---|---|---|---|
| 79 | 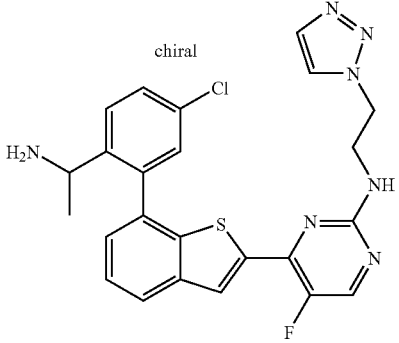 | N-(2-(1H-1,2,3-Triazol-1-yl)ethyl)-4-(7-(2-(1-aminoethyl)-5-chlorophenyl)benzo[b]thiophen-2-yl)-5-fluoropyrimidin-2-amine | 494 | Chiralpak ® AD-H First fraction |
| 80 | 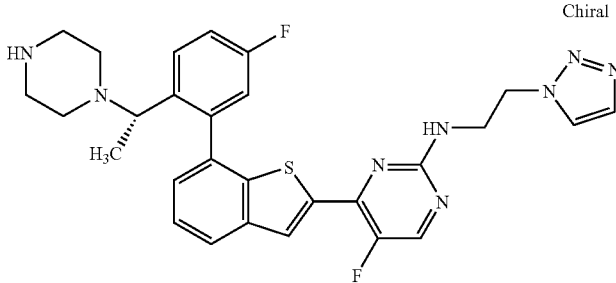 | (S)-N-(2-(1H-1,2,3-Triazol-1-yl)ethyl)-5-fluoro-4-(7-(5-fluoro-2-(1-(piperazin-1-yl)ethyl)phenyl)benzo[b]thiophen-2-yl)pyrimidin-2-amine | 547 | Chiralpak ® AD-H |
| 81 | 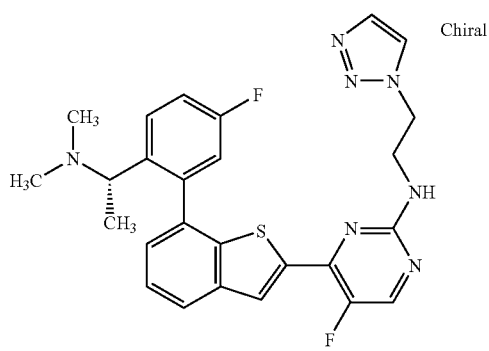 | (S)-N-(2-(1H-1,2,3-Triazol-1-yl)ethyl)-4-(7-(2-(1-(dimethylamino)ethyl)-5-fluorophenyl)benzo[b]thiophen-2-yl)-5-fluoro-pyrimidin-2-amine | 506 | Chiralpak ® AD-H |
| 82 | 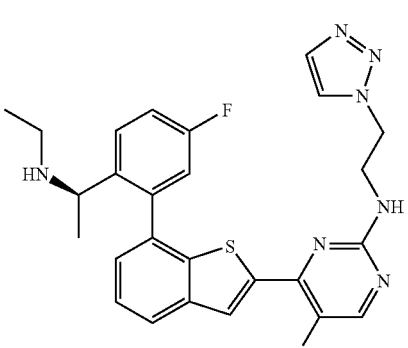 | (S)-N-(2-(1H-1,2,3-Triazol-1-yl)ethyl)-4-(7-(2-(1-(ethylamino)ethyl)-5-fluorophenyl)benzo[b]thiophen-2-yl)-5-fluoro-pyrimidin-2-amine | 506 | Chiralpak ® AD-H |

-continued

| Ex | Compound structure | Compound Name | MS (ES) m/z [M + 1]+ | Comments |
|---|---|---|---|---|
| 83 | 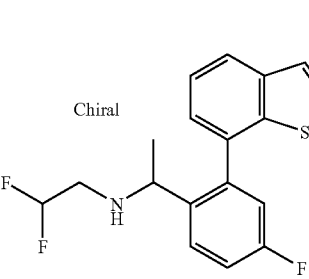 | N-(2-(1H-1,2,3-Triazol-1-yl)ethyl)-4-(7-(2-(1-(2,2-difluoroethylamino)ethyl)-5-fluorophenyl)benzo[b]thiophen-2-yl)-5-fluoro-pyrimidin-2-amine | 542 | Chiralpak® AS-H Second fraction |
| 84 | 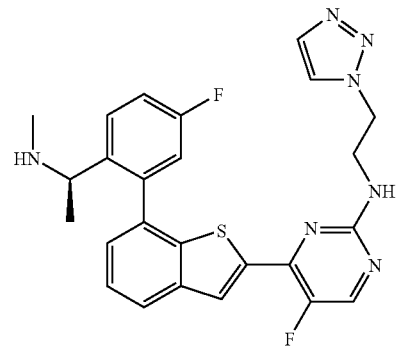 | (R)-N-(2-(1H-1,2,3-Triazol-1-yl)ethyl)-5-fluoro-4-(7-(5-fluoro-2-(1-(methylamino)ethyl)-phenyl)benzo[b]thiophen-2-yl)pyrimidin-2-amine | 492 | Chiralpak® AD-H |
| 85 | 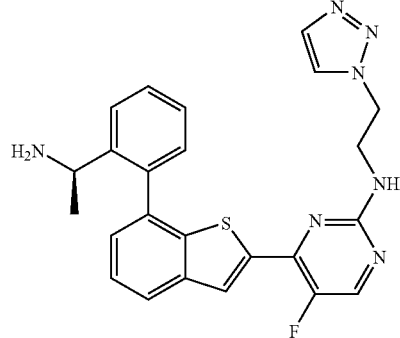 | (R)-N-(2-(1H-1,2,3-Triazol-1-yl)ethyl)-4-(7-(2-(1-aminoethyl)phenyl)-benzo[b]thiophen-2-yl)-5-fluoropyrimidin-2-amine | 460 | Chiralcel® OD-H column |
| 86 | 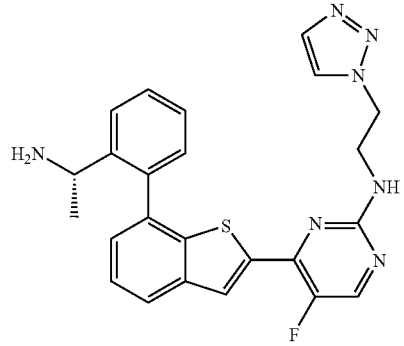 | (S)-N-(2-(1H-1,2,3-Triazol-1-yl)ethyl)-4-(7-(2-(1-aminoethyl)phenyl)-benzo[b]thiophen-2-yl)-5-fluoropyrimidin-2-amine | 460 | Chiralcel® OD-H |

-continued

| Ex | Compound structure | Compound Name | MS (ES) m/z [M + 1]+ | Comments |
|---|---|---|---|---|
| 87 | 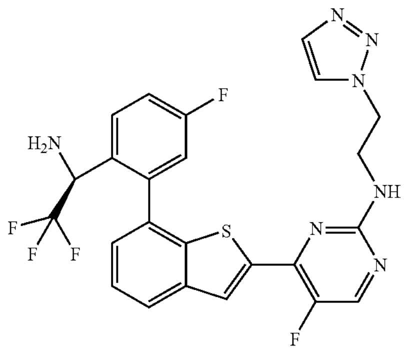 | (S)-N-(2-(1H-1,2,3-Triazol-1-yl)ethyl)-4-(7-(2-(1-amino-2,2,2-trifluoro-ethyl)-5-fluorophenyl)-benzo[b]thiophen-2-yl)-5-fluoropyrimidin-2-amine | 532 | Chiralpak ® AD-H |
| 88 | 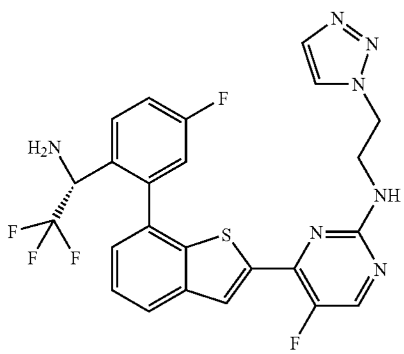 | (R)-N-(2-(1H-1,2,3-Triazol-1-yl)ethyl)-4-(7-(2-(1-amino-2,2,2-trifluoro-ethyl)-5-fluorophenyl)-benzo[b]thiophen-2-yl)-5-fluoropyrimidin-2-amine | 532 | Chiralpak ® AD-H |
| 89 | 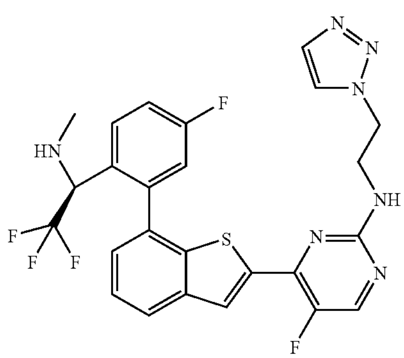 | (S)-N-(2-(1H-1,2,3-Triazol-1-yl)ethyl)-5-fluoro-4-(7-(5-fluoro-2-(2,2,2-trifluoro-1-(methyl-amino)ethyl)phenyl)-benzo[b]thiophen-2-yl)-pyrimidin-2-amine | 546 | Chiral OJ-H |
| 90 | 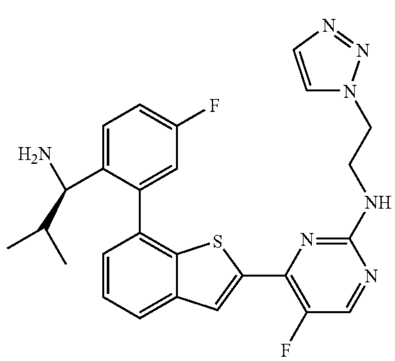 | (R)-N-(2-(1H-1,2,3-Triazol-1-yl)ethyl)-4-(7-(2-(1-amino-2-methylpropyl)-5-fluorophenyl)benzo[b]thiophen-2-yl)-5-fluoro-pyrimidin-2-amine | 506 | Chiralpak ® AS-H |

| Ex | Compound structure | Compound Name | MS (ES) m/z [M + 1]+ | Comments |
|---|---|---|---|---|
| 91 | 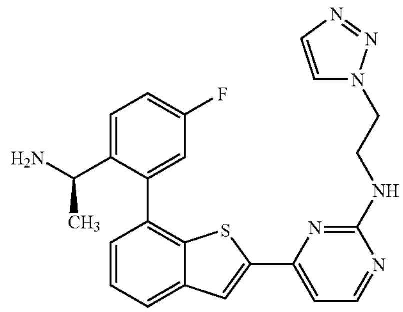 | (R)-N-(2-(1H-1,2,3-Triazol-1-yl)ethyl)-4-(7-(2-(1-aminoethyl)-5-fluorophenyl)benzo[b]thiophen-2-yl)pyrimidin-2-amine | 460 | Chiralcel ® OJ-H |
| 92 | 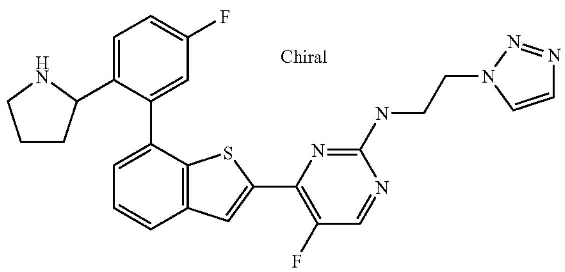 | (N-(2-(1H-1,2,3-Triazol-1-yl)ethyl)-5-fluoro-4-(7-(5-fluoro-2-(pyrrolidin-2-yl)phenyl)benzo[b]thiophen-2-yl)pyrimidin-2-amine | 504 | Chiralcel ® OJ-H First fraction |

*the absolute configuration of some enantiomers in this table are not deteremined.
*for example, enantiomer examples 76-79, 83, and 92 are specified by retention time, i.e., first or second fraction off column.

EXAMPLE 93

N-(2-(1H-1,2,3-Triazol-1-yl)ethyl)-4-(7-(2-(2-aminopropan-2-yl)-5-fluorophenyl)benzo[b]thiophen-2-yl)-5-fluoropyrimidin-2-amine Heat a mixture of N-(2-(2-(2-(2-(2-(1H-1,2,3-triazol-1-yl)ethylamino)-5-fluoropyrimidin-4-yl)benzo[b]thiophen-7-yl)-4-fluorophenyl)propan-2-yl)formamide (120 mg, 231 μmol) and sodium hydroxide (5 N, 10 mL, 50 mmol) in ethanol (10 mL) at 80° C. for 3 h. Dilute the mixture with ice water and extract with chloroform/IPA (3/1, 100 mL). Wash the organic phase with water/aqueous saturated sodium chloride, dry over sodium sulfate, and concentrate in vacuo. Purify the crude product by FCC (DCM to chloroform/methanol/ammonium hydroxide 7/3/0.05 as gradient) to give the title compound as a grey solid (82 mg, 75%). MS (ES) m/z 492 [M+1]+.

EXAMPLE 94

2-(2-(2-(2-(2-(1H-1,2,3-Triazol-1-yl)ethylamino)-5-fluoropyrimidin-4-yl)benzo[b]thiophen-7-yl)-4-fluorophenyl)-2-methylpropanamide

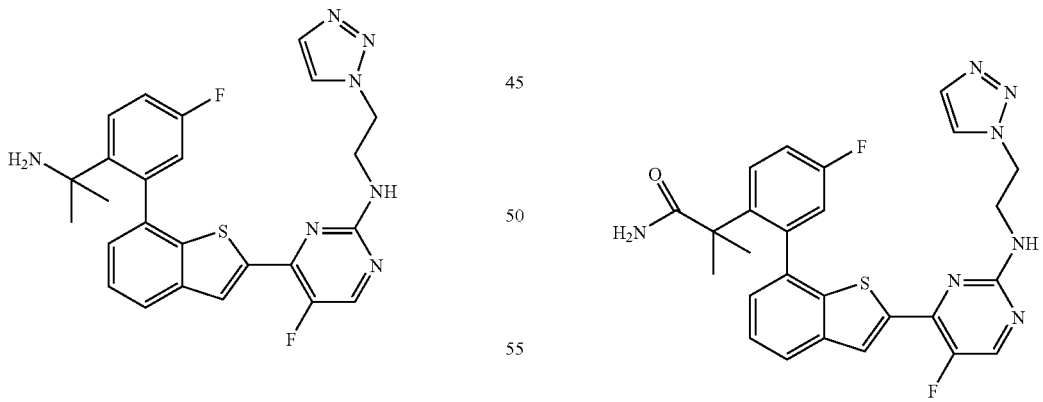

Add hydrogen peroxide to a stirred solution of 2-(2-(2-(2-(2-(1H-1,2,3-triazol-1-yl)ethylamino)-5-fluoropyrimidin-4-yl)benzo[b]thiophen-7-yl)-4-fluorophenyl)-2-methylpropanenitrile (140 mg, 279 μmol), 1,4,7,10,13,16-hexaoxacyclooctadecane (14 mg, 1% wt), and sodium carbonate (1 M, 5 mL, 5 mmol) in 10 mL ethanol drop wise. Stir the mixture at RT for 48 h. Dilute the reaction mixture with water and extract with DCM. Dry the organic phase over sodium sulfate and concentrate in vacuo. Purify the crude product by FCC (10% methanol in DCM as elute) to give the title compound as a yellow solid (110 mg, 76%). MS (ES) m/z 520 [M+1]+.

EXAMPLE 95

(R)—N—((R)-1-(2-(2-(2-(2-(1H-1,2,3-Triazol-1-yl)ethylamino)-5-fluoropyrimidin-4-yl)benzo[b]thiophen-7-yl)-4-fluorophenyl)ethyl)-2-aminopropanamide

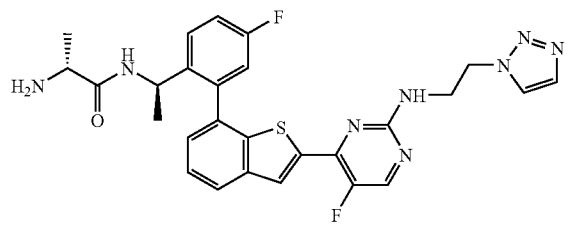

Dissolve {1-[1-(4-fluoro-2-{2-[5-fluoro-2-(2-[1,2,3]triazol-1-yl-ethylamino)-pyrimidin-4-yl]-benzo[b]thiophen-7-yl}-phenyl)-ethylcarbamoyl]-ethyl}-carbamic acid 9H-fluoren-9-ylmethyl ester (129 mg, 167 µmol) in piperidine (5 mL). Stir the mixture at RT for 30 min and then dilute with chloroform/IPA (3/1, 100 mL). Wash the organic phase with water/aqueous saturated sodium chloride, dry over sodium sulfate, and concentrate in vacuo. Purify the crude product by FCC (10% methanol in DCM to chloroform/methanol/ammonium hydroxide (7/3/0.05) as a gradient to give the title compound as a yellow solid (72 mg, 78%). MS (ES) m/z 549 [M+1]+.

EXAMPLE 96

Chiral Synthesis of Example 88

(R)—N-(2-(1H-1,2,3-Triazol-1-yl)ethyl)-4-(7-(2-(1-amino-2,2,2-trifluoroethyl)-5-fluorobenzyl)benzo[b]thiophen-2-yl)-5-fluoropyrimidin-2-amine

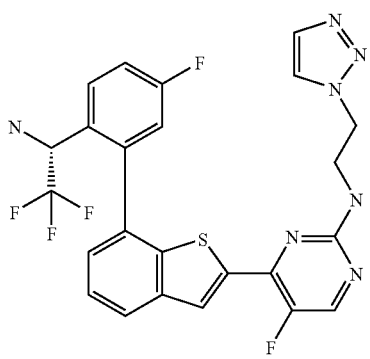

A. (S,E)-N-(1-(2-Bromo-4-fluorophenyl)ethylidene)-2-methylpropane-2-sulfinamide

Add (S)-(−)-2-methyl-2-propanesulfinamide (15 g, 73.89 mmol) to a stirring mixture of 2-bromo-4-fluorobenzaldehyde (9.85 g, 81.28 mmol) in 1,2-dichloroethane (50 mL) at RT. And then add Ti(OEt)$_4$ (25.28 g, 4.78 mol) to the mixture and stir overnight at RT. Cool the reaction in an ice/water bath, and dilute with water. Filter the reaction mixture over a ½ inch pad of celite, and wash the filtered stuff with dichloromethane (4×150 mL). Separate the organic layer and wash the aqueous layer with 150 mL DCM. Combine the organic layers, dry over MgSO$_4$, filter, and concentrate. Purify the residue via silica chromatography eluting with hexanes to 8:2 hexanes:ethyl acetate. Pool the desired fractions and concentrate to give the product as a very pale yellow oil (21.5 g, 95%). GCMS m/z 305 [M]+.

B. (S)—N—((R)-1-(2-Bromo-4-fluorophenyl)-2,2,2-trifluoroethyl)-2-methylpropane-2-sulfinamide Add tetrabutylammonium triphenyldifluorosilicate (29.8 g, 55.19 mmol) to a stirring mixture of (S,E)-N-(1-(2-bromo-4-fluorophenyl)ethylidene)-2-methylpropane-2-sulfinamide (13 g, 42.46 mmol) in THF. Cool the mixture to about −60° C. and add the (trifluoromethyl)trimethylsilane over about 10 min. Warm up to −55° C. and stir for 2 h. Continue to warm up to 0° C. Cool the mixture back to −30° C., and quench with saturated NH$_4$Cl (150 mL). Extract product into ethyl acetate (2×200 mL). Combine extracts, wash with aqueous saturated sodium chloride, dry over Na$_2$SO$_4$, filter, and concentrate. Purify the material on 700 g silica eluting with 8:2 to 1:1 hexanes:ethyl acetate to a crude material. Crystallize the material to give long needles (9.7 g, 91%). MS (ES) m/z 377 [M+1]+.

C. (S)—N—((R)-1-(2-((2-(2-(2-(1H-1,2,3-Triazol-1-yl)ethylamino)-5-fluoropyrimidin-4-yl)benzo[b]thiophen-7-yl)methyl)-4-fluorophenyl)-2,2,2-trifluoroethyl)-2-methylpropane-2-sulfinamide Prepare the title compound with procedures similar to those described for N-(2-(1H-1,2,3-Triazol-1-yl)ethyl)-5-fluoro-4-(7-(5-fluoro-1H-indol-7-yl)benzo[b]thiophen-2-yl)pyrimidin-2-amine.

D. (R)—N-(2-(1H-1,2,3-Triazol-1-yl)ethyl)-4-(7-(2-(1-amino-2,2,2-trifluoroethyl)-5-fluorobenzyl)benzo[b]thiophen-2-yl)-5-fluoropyrimidin-2-amine Stir a mixture of (S)—N—((R)-1-(2-((2-(2-(2-(1H-1,2,3-Triazol-1-yl)ethylamino)-5-fluoropyrimidin-4-yl)benzo[b]thiophen-7-yl)methyl)-4-fluorophenyl)-2,2,2-trifluoroethyl)-2-methylpropane-2-sulfinamide (10.5 g, 16.52 mmol) and HCl (16.52 mL, 66.07 mmol, in dioxane) in methanol (100 mL) for 2 h. Concentrate the mixture and dilute with NaOH (1 N). Extract the product with ethyl acetate (150 mL×3). Wash the organic layer with 1:1 water/aqueous saturated sodium chloride and aqueous saturated sodium chloride. Dry over Na$_2$SO$_4$, filter, and concentrate. Dissolve the material with heat in DCM/hexanes and solidify the material in 3 h upon cooling. Filter the solid to give the title compound (8.1 g tan solid, 92%). MS (ES) m/z 546 [M+1]+.

Plk1 has been shown to be over expressed in many human tumors, such as non-small cell lung, oropharyngeal, esophageal, gastric, melanoma, breast, ovarian, endometrial, colorectal, glioblastoma, papillary, pancreatic, prostate, hepatoblastoma and non-Hodgkin lymphoma cancers. Furthermore, Plk1 expression has prognostic significance in non-small cell lung, oropharyngeal, esophageal, melanoma, colorectal, hepatoblastoma and non-Hodgkin lymphoma cancers (Strebhardt, K. and A. Ullrich. *Nature Reviews Cancer* 6(4): 321-30 (2006)). Plk1 phosphorylated substrates regulate progression of mitosis by coordinating centrosome maturation, entry into mitosis, sister chromatid separation and cytokinesis [Eckerdt F. Strebhardt K. Cancer Research. 66(14):6895-8, 2006; Strebhardt and Ullrich 2006; van de Weerdt, B. C. and R. H. Medema. *Cell Cycle* 5(8): 853-64 (2006)]. Inhibiting Plk1 function using antibody injection, expression of a dominant negative Plk1, and antisense mRNA reduction produces monopole spindles and anaphase arrest leading to mitotic cell death in tumor cell lines but reversible G2 arrest in normal non-transformed primary cell lines.

Additionally, it has been reported that Plk may be useful in the treatment of rhabdoid tumors, (Morozov A., et al., Clinical Cancer Research. 13(16):4721-30, (Aug. 15, 2007).

BI-2536 has demonstrated activity in preclinical models using HCT116, A549 and NCIH460 murine xenografts (Baum, A., P. Garin-Chesa, et al. (2006). #C191 In vivo activity of BI 2536, a potent and selective inhibitor of the mitotic kinase PLK1, in a range of cancer xenografts. AACR-NCI-EORTC International Conference on "Molecular Targets and Cancer Therapeutics", Philadelphia, Pa.).

The results of the following assays demonstrate evidence that the compounds of the present invention are useful as anticancer agents. Certain of the example compounds described herein are racemic mixtures. These compounds are tested as racemic mixtures and/or as individual enantiomers. At least one enantiomer or the racemate met the assay criterion below.

Expression and Purification of Plk1

Human Plk1 cDNA may be directly linked at one of its termini with a polynucleotide sequence expressing a $His_6$ tag, such as the C-terminal FLAG-$His_6$ tag, and inserted into an appropriate expression vector, such as a pFastBac™ vector (Invitrogen) and transfected into an appropriate system, such as baculovirus similar to what has been reported by Yue-Wei Qian, et al., Science, 282, 1701 (1998) for xPlkk1. If a viral expression system is used, then the virus (e.g., baculovirus bearing a Plk1-Flag-$His_6$ tag polynucleotide construct) is infected into a culture of a suitable host cell, such as Sf9 cells. When sufficient amounts of the Plk1-Flag-$His_6$ tag fusion protein have been expressed, for example, at about 46 hours after infection, the culture should be treated with okadaic acid (0.1 µM) for a sufficient period of time (e.g., 3 hours). The Plk1-Flag-$His_6$ tag fusion is purified from cell pellets using a metal affinity resin, such as TALON™ using methods well known in the art. Purified Plk1-Flag-$His_6$ tag fusion is stored in a suitable medium, such as 10 mM HEPES, 150 mM NaCl, 0.01% TRITON® X-100, 1 mM dithiothreitol (DTT), 10% glycerol, pH 7.5, at −80° C. in small aliquots until use. The identity of the purified Plk1-Flag-$His_6$ tag fusion protein is confirmed by MALDI (Matrix-Assisted Laser Desorption/Ionization).

Expression and Purification of GST-Cdc25C(1-206)

Human Cdc25C cDNA, which may be obtained from any appropriate source, may be expressed in any convenient expression system, after which purification is effected by well known methods similar to that described by Bin Ouyang et al, Oncogene, 18, 6029-6036 (1999). One convenient system involves overnight growth at 18° C. of E.coli BL21 transformed with the pGEX-2T vector (Amersham) into which the cDNA for human Cds25C has been engineered for induced expression using 1 mM isopropyl-beta-D-thiogalactopyranoside. The expressed GST-Cdc25C(1-206), the substrate for Plk1, may be purified (for example, by GLUTATHIONE SEPHAROSE® 4B) and stored in an appropriate solution, such as 10 mM HEPES, 100 mM NaCl, pH 7.5 in small aliquots at −80° C.

Plk1 Inhibition Assay

Plk1 kinase reactions contain Plk1-Flag-$His_6$ tag fusion enzyme (0.2 ng/µL) in a buffer containing 50 mM HEPES, pH 7.3, 1.0 mM dithiothreitol, 5.0 µM ATP, 10 mM $MgCl_2$, 0.01% TRITON® X-100, 0.4 µCi $^{33}P$-ATP, and 0.06 µg/mL GST-Cdc25c (1-206) peptide. Compounds are provided as 10 mM stocks in DMSO. Compounds are serially diluted 1:3 in 20% DMSO to create a 10-point concentration-response curve and subsequently are diluted 1:5 (20 µM to 0.001 µM final in 4% final DMSO concentration) in the reaction mixture to determine compound activity. The reaction is carried out at room temperature for 60 min and then quenched by adding 60 µL of 10.0% $H_3PO_4$. The reaction mixture (85 µL) is transferred to a 96 well phosphocellulose filter plate pre-wetted with 30 µL of 10.0% $H_3PO_4$, incubated at room temperature for 20-30 min and then washed 3× with 0.5% $H_3PO_4$. Wells are dried before addition of 40 µL of MicroScint™20 (Packard) and then counted on a Wallac MICROBETA® Jet. The percentage inhibition values from the 10-point concentration response data are subsequently analyzed, for example, using ACTIVITY BASE™ software (IDBS), using a 4-parameter logistic equation. Absolute $IC_{50}$ values are calculated from the resulting curve fit. All exemplified compounds have an $IC_{50}$ less than 100 nM with a Minimum Significant Ratio (MSR) for the $IC_{50}$ of 3.6, with the caveat that either the racemic mixture and/or at least one enantiomer had an $IC_{50}$ less than 100 nM. For example, Example 57 racemate has an $IC_{50}$ of 11 nM. This demonstrates that the compounds of the present invention are potent inhibitors of Plk1.

pHH3(S10), Mitotic Cells, and DNA Content Assays

HeLa Cells are plated at 200 cells/well in 96 well Beckman Dickinson BIOCOAT™ plates, and are incubated in MEM (Minimum Essential Medium) with 10% FBS (Fetal Bovine Serum) in 37° C., 5% $CO_2$ for 24 hours. Cells are treated by adding compound (in 0.25% DMSO) to the medium, dosing at 10 points across the range 0.5 µM to 0.0098 µM. After 23 hours exposure to the compounds, cells are fixed, for example with the PREFER™ fixative for 30 min then are permeablized with 0.1% TRITON® X100 in phospate buffered saline (PBS) solution for 15 min. Cells are washed 3 times with PBS then digested with 50 µg/mL RNAse. Primary antibody, anti-phosphohistone H3 Serine 10, is added at 1:500 in PBS with 1% bovine serum albumin (BSA) to the cells over night at 4° C. After 3 PBS washes, cells are incubated with Alexa488 labeled secondary antibody for 1 hour at room temperature. Again they are washed 3 times with PBS, and then 15 µM propidium iodide is added for 30 min to stain nuclei. Fluorescence Plates are scanned with ACUMEN EXPLORER™ [Laser-scanning fluorescence microplate cytometer (comprising of 488 nm argon ion laser excitation and multiple photomultiplier tube detection), manufactured by TTP LABTECH LTD] to measure phosphohistone H3, DNA content and mitotic cells as measured by DNA condensation. Image analysis are based on cellular fluorescent signals for identifying cells in different subpopulations. pHH3 (S10) positive cells are identified by mean intensity at 500-530 nm above the threshold. Total intensity at 655-705 nm from propidium iodide/DNA is used to identify individual cells (cells with DNA content from 2N to 4N) and subpopulations in cell cycle (2N cells, 4N cells). Peak intensity at 575-640 nm is used to identify DNA condensation that is used as the marker to identify mitotic cells among 4N cells. Assay outputs are percentage of each identified subpopulations, % pHH3, % 2N, % 4N, % mitotic and total cell number. The $EC_{50}$ is determined by curve fitting to a four parameter logistic for each output using ACTIVITY BASE™. The resulting $EC_{50}$s for PHH3(s10), DNA content, and mitotic have a Minimum Significant Ratio (MSR) of 2.6, 2.4 and 2.5, respectively. For example, Example 57 racemate has an pHH3(s10) $EC_{50}$=37 nM, DNA content $EC_{50}$=40 nM and mitotic $EC_{50}$=36 nM.

Antiproliferative Assay

The effects of compounds on cell proliferation can be determined using cells and cell proliferation methods well-known in the art (Robert C. Squatrito et al., Gynecological Oncology, 58, 101-105, (1995)). For example, HCT116 cells, which may be obtained from the American Type Culture Collection, may be seeded at ~2000 cells/well in 96-well plates and allowed to attach overnight in a humidified $CO_2$ incubator at 37° C. Following the 20-24 hour incubation, half-log serially diluted compounds are added and the plates are returned to the incubator. After an appropriate length of exposure (e.g., 72 hours), cell proliferation is estimated using well-known methods. In one method, 10 µL of a tetrazolium salt, such as Alamar Blue™ is added to the cell plates. After an appropriate exposure to the dye, fluorescence (530 nm excitation, 580 nm emission) is determined The resulting $IC_{50}$ has a Minimum Significant Ratio (MSR) of 3.1. For example, Example 57 racemate has an average $IC_{50}$ of 119 nM (n=2). This demonstrates that the compounds of the present invention are useful in treating proliferative disorders, including types of cancer.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (A. Gennaro, et al., eds., 19th ed., Mack Publishing Co., 1995).

The compounds of Formula I are generally effective over a wide dosage range. For example, dosages per day normally fall within the range of about 1 to about 10 mg/kg of body weight, preferably 2 to 6.5 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

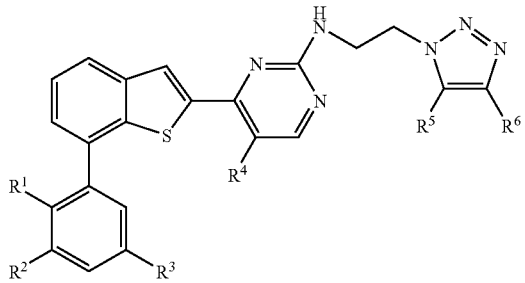

wherein:
$R^1$ is methyl, methoxy, hydroxy, amino, chloro, amino($C_1$-$C_4$ alkyl), dimethylamino($C_1$-$C_2$ alkyl), ($C_1$-$C_2$ alkyl)amino($C_1$-$C_2$ alkyl), aminocarbonyl($C_1$-$C_3$ alkyl), 1-((1-amino)ethylcarbonylamino)ethyl, 2-(N-methylamino)ethoxy, 2-cyanoprop-2-yl, (2-hydroxy-2-methyl)-1-propyloxy, (2-hydroxy)ethylaminocarbonylmethyl, (1-fluoro)-(2-amino)ethyl, (1-fluoro)-(1-methyl)-(2-amino)ethyl, difluoromethyl, 1-((2,2-difluoro)ethylamino)ethyl, difluoromethylcarbonyl, trifluoromethylcarbonyl, (1-amino)-(2,2,2-trifluoro)ethyl, (1-methylamino)-(2,2,2-trifluoro)ethyl, (1-hydroxy)-(2,2,2-trifluoro)ethyl, 2-(amino)ethoxy, 2-(hydroxy)ethoxy, 1-((N-(2-hydroxy)ethyl)-(N-methyl)-amino)($C_1$-$C_2$ alkyl), 4-(hydroxy)piperidin-1-yl-methyl, 1-(piperazin-1-yl)ethyl, 2-(hydroxy)ethylsulfonyl, 1-(amino)cyclopropyl, 1-(methylamino)cyclopropyl, 1-amino(cyclobutyl), 1-aminocyclopent-2-yl, cyclopentanone-2-yl, tetrahydrofur-2-yl, pyrrolidin-2-yl, aziridin-2-yl, or (morpholin-4-yl)methyl;
$R^2$ is hydrogen or amino provided that if $R^2$ is amino, $R^1$ and $R^2$ form a pyrrole ring fused to the phenyl; or if $R^1$ is amino, $R^1$ and $R^2$ can form either a pyrrole or a pyridine ring fused to the phenyl;
$R^3$ is hydrogen, chloro, or fluoro;
$R^4$ is hydrogen, methyl, chloro, or fluoro;
$R^5$ is hydrogen, hydroxymethyl, or methyl; and
$R^6$ is hydrogen, hydroxymethyl, or methyl; or
a pharmaceutically acceptable salt thereof.
2. The compound according to claim 1 wherein:
$R^1$ is amino($C_1$-$C_4$ alkyl), dimethylamino($C_1$-$C_2$ alkyl), ($C_1$-$C_2$ alkyl)amino($C_1$-$C_2$ alkyl), aminocarbonyl($C_1$-$C_3$ alkyl), 1-((1-amino)ethylcarbonylamino)ethyl, 2-cyanoprop-2-yl, (2-hydroxy)ethylaminocarbonylmethyl, (1-fluoro)-(2-amino)ethyl, (1-fluoro)-(1-methyl)-(2-amino)ethyl, difluoromethyl, 1-((2,2-difluoro)ethylamino)ethyl, (1-amino)-(2,2,2-trifluoro)ethyl, (1-methylamino)-(2,2,2-trifluoro)ethyl, (1-hydroxy)-(2,2,2-trifluoro)ethyl, 1-((N-(2-hydroxy)ethyl)-(N-methyl)-amino)($C_1$-$C_2$ alkyl), 4-(hydroxy)piperidin-1-yl-methyl, 1-(piperazin-1-yl)ethyl, or (morpholin-4-yl)methyl; or
a pharmaceutically acceptable salt thereof.
3. The compound according to claim 1 wherein:
$R^1$ is amino($C_1$-$C_4$ alkyl), dimethylamino($C_1$-$C_2$ alkyl), ($C_1$-$C_2$ alkyl)amino($C_1$-$C_2$ alkyl), (2-hydroxy)ethylaminocarbonylmethyl, or (morpholin-4-yl)methyl; and
$R^6$ is hydrogen; or
a pharmaceutically acceptable salt thereof.

4. The compound according to claim 1 wherein:

$R^1$ is amino($C_1$-$C_4$ alkyl), dimethylamino($C_1$-$C_2$ alkyl), ($C_1$-$C_2$ alkyl)amino($C_1$-$C_2$ alkyl), or (morpholin-4-yl)methyl;

$R^3$ is fluoro;

$R^4$ is fluoro;

$R^5$ is hydrogen or methyl; and $R^6$ is hydrogen; or a pharmaceutically acceptable salt thereof.

5. The compound according to claim 1 wherein:

$R^1$ amino($C_1$-$C_4$ alkyl), dimethylamino($C_1$-$C_2$ alkyl), or ($C_1$-$C_2$ alkyl)amino($C_1$-$C_2$ alkyl);

$R^3$ is fluoro;

$R^4$ is fluoro;

$R^5$ is hydrogen or methyl; and $R^6$ is hydrogen; or a pharmaceutically acceptable salt thereof.

6. The compound according to claim 1 wherein $R^1$ is 1-(amino)ethyl, $R^2$ is hydrogen, $R^3$ is fluoro, $R^4$ is fluoro, $R^5$ is hydrogen, and $R^6$ is hydrogen, or a pharmaceutically acceptable salt thereof.

7. The compound according to claim 1 wherein $R^1$ is 1-(amino)ethyl, $R^2$ is hydrogen, $R^3$ is fluoro, $R^4$ is fluoro, $R^5$ is methyl, and $R^6$ is hydrogen, or a pharmaceutically acceptable salt thereof.

8. A pharmaceutical composition comprising a compound of claim 1 or a pharmaceutically acceptable salt thereof, in combination with a pharmaceutically acceptable carrier, diluent or excipient.

* * * * *

UNITED STATES PATENT AND TRADEMARK OFFICE
CERTIFICATE OF CORRECTION

| | |
|---|---|
| PATENT NO. | : 8,063,035 B2 |
| APPLICATION NO. | : 12/598926 |
| DATED | : November 22, 2011 |
| INVENTOR(S) | : Joyce Z. Crich et al. |

It is certified that error appears in the above-identified patent and that said Letters Patent is hereby corrected as shown below:

At Column 80, Line 56: In Claim 2, delete "2 -" and insert -- 2- --, therefor.

Signed and Sealed this
Tenth Day of January, 2012

David J. Kappos
*Director of the United States Patent and Trademark Office*